United States Patent
Hogg et al.

(10) Patent No.: US 11,972,864 B2
(45) Date of Patent: *Apr. 30, 2024

(54) PRE-EMPTIVE CHRONIC OBSTRUCTIVE PULMONARY DISEASE RISK NOTIFICATIONS BASED ON MEDICAMENT DEVICE MONITORING

(71) Applicant: Reciprocal Labs Corporation (dba Propeller Health), Madison, WI (US)

(72) Inventors: Christopher Hogg, San Francisco, CA (US); Gregory F. Tracy, Madison, WI (US); John David Van Sickle, Oregon, WI (US); Jason Grosz, Middleton, WI (US); Jeffrey J. Alexander, Madison, WI (US); Chase Acton, Alameda, WI (US); Mike Lohmeier, Sun Prairie, WI (US); John Kalmi, Wauwatosa, WI (US); Dmitry Stupakov, Cupertino, CA (US)

(73) Assignee: Reciprocal Labs Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/177,099

(22) Filed: Feb. 16, 2021

(65) Prior Publication Data

US 2021/0272685 A1  Sep. 2, 2021
US 2023/0207113 A9  Jun. 29, 2023

Related U.S. Application Data

(63) Continuation of application No. 15/293,851, filed on Oct. 14, 2016, now Pat. No. 10,957,447.

(Continued)

(51) Int. Cl.
*G16H 40/63* (2018.01)
*G16H 10/60* (2018.01)
(Continued)

(52) U.S. Cl.
CPC ............ *G16H 40/63* (2018.01); *G16H 10/60* (2018.01); *G16H 20/10* (2018.01); *G16H 50/30* (2018.01)

(58) Field of Classification Search
CPC ........ G16H 40/63; G16H 10/60; G16H 50/30; G16H 20/10
(Continued)

(56) References Cited

U.S. PATENT DOCUMENTS

2006/0071011 A1  4/2006  Varvarelis et al.
2008/0015893 A1*  1/2008  Miller ................... G16H 70/40
                                                        600/300

(Continued)

FOREIGN PATENT DOCUMENTS

WO   WO 2015/178907 A1   11/2015

OTHER PUBLICATIONS

United States Office Action, U.S. Appl. No. 15/293,851, filed May 4, 2020, 21 pages.
(Continued)

*Primary Examiner* — Michael Tomaszewski
(74) *Attorney, Agent, or Firm* — McDermott Will & Emery LLP

(57) ABSTRACT

A system and method for providing chronic obstructive pulmonary disease (COPD) exacerbation risk notifications in real time or near-real time is described. Rescue and controller medication events are detected by sensors associated with the patient's medicament device/s, and provide a basis to determine to rescue and controller medication use trends for the patient. This data is analyzed to determine the patient's risk for COPD exacerbation after each event, and is used to send notifications to one or both of the patient and their health care provider.

20 Claims, 23 Drawing Sheets

COPD Analytics System
100

Related U.S. Application Data

(60) Provisional application No. 62/242,095, filed on Oct. 15, 2015.

(51) Int. Cl.
*G16H 20/10* (2018.01)
*G16H 50/30* (2018.01)

(58) Field of Classification Search
USPC .......................................................... 705/2–3
See application file for complete search history.

(56) References Cited

U.S. PATENT DOCUMENTS

| | | |
|---|---|---|
| 2008/0015894 A1 | 1/2008 | Miller et al. |
| 2008/0097784 A1* | 4/2008 | Miller .................... G16H 70/40 |
| | | 705/2 |
| 2008/0126131 A1* | 5/2008 | Lou ........................ G16H 20/10 |
| | | 705/3 |
| 2009/0194104 A1 | 8/2009 | Van Sickle |
| 2014/0365139 A1 | 12/2014 | Criner |

OTHER PUBLICATIONS

United States Office Action, U.S. Appl. No. 15/293,851, filed Dec. 31, 2019, 15 pages.

* cited by examiner

FIG. 30

Tips - smells or scents

Create a "scent free" home. This means perfumes, air fresheners, laundry detergents, lotions and shampoo.

Is this interesting?

| Yes | No |

310z

Tips - tobacco

Tobacco smoke is the #1 asthma trigger. Avoid smoking or second hand smoke at all costs. If you smoke, consider a program to help you quit. Do not allow smoking in your home or in the car.

Is this interesting?

| Yes | No |

310aa
Time Of Day Trend
100% of your events occur during the Afternoon.
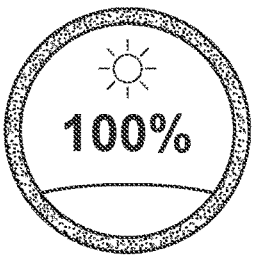
310bb
Symptom Trend
You reported that 67% of your events display the symptom Chest Tightness.
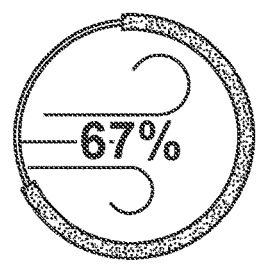
310cc
Day of Week Trend
100% of your events occur on Monday.
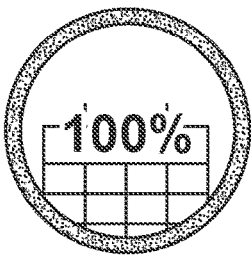
310dd
Trigger Trend
You reported that 33% of your events were triggered by Smells or Scents.
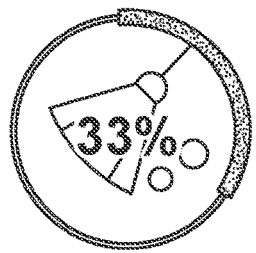
FIG. 3Q

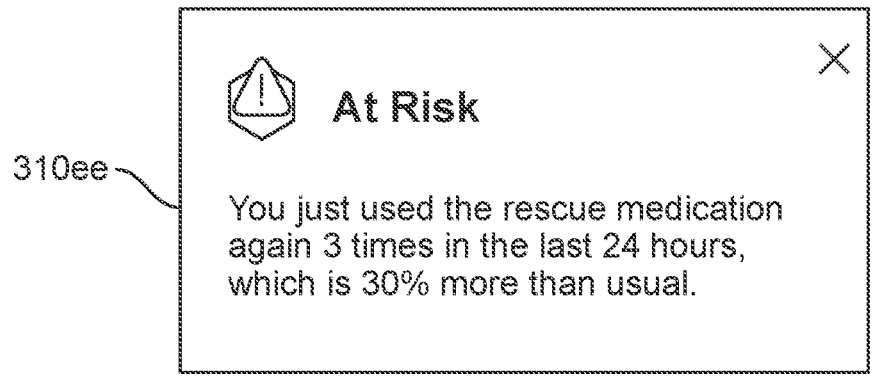
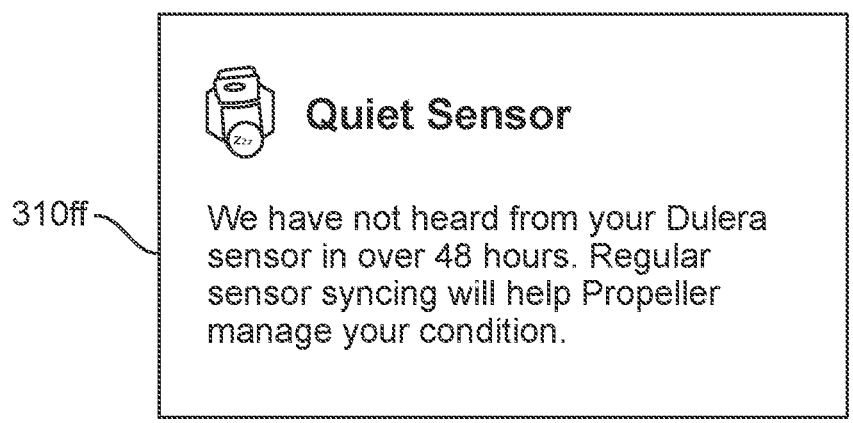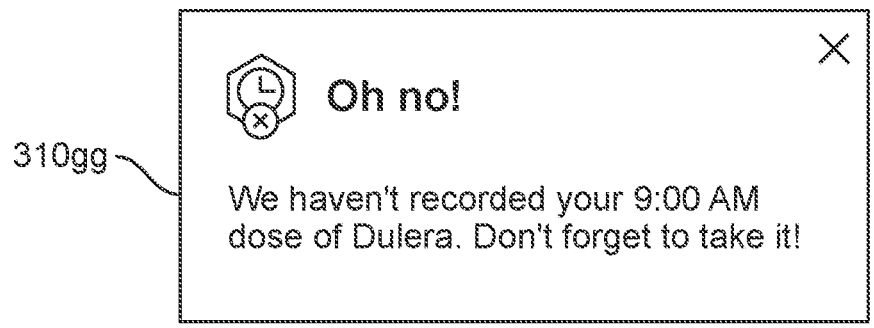
FIG. 3R

PRE-EMPTIVE CHRONIC OBSTRUCTIVE PULMONARY DISEASE RISK NOTIFICATIONS BASED ON MEDICAMENT DEVICE MONITORING

CROSS-REFERENCE TO RELATED APPLICATION

This application is a continuation of co-pending U.S. patent application Ser. No. 15/293,851, filed on Oct. 14, 2016, which claims the benefit of U.S. Provisional Application No. 62/242,095, filed Oct. 15, 2015, both of which are incorporated by reference herein in their entirety for all purposes.

BACKGROUND

Field of Art

The disclosure relates generally to inhalers, and more specifically to monitoring medicament device usage in relation to chronic obstructive pulmonary disease (COPD).

Description of the Related Art

Chronic obstructive pulmonary disease (COPD) is a significant and costly public health problem. Recent studies by the Centers for Disease Control and Prevention have listed COPD as the third leading cause of death in the United States while estimating close to 13 million people may have COPD induced impaired lung function. Despite the development of new medications, rates of hospitalizations and emergency room visits are not decreasing; each year in the United States the disease causes approximately 715,000 hospitalizations, and 134,000 deaths. Additionally, the cost to the nation for COPD was recently projected to be approximately $49.9 billion, including $29.5 billion in direct health care expenditures, $8.0 billion in indirect morbidity costs and $12.4 billion in indirect mortality costs.

Nearly all persons with COPD carry an inhaled medication to immediately relieve symptoms whenever or wherever they occur. The frequency and location with which patients use these medications are important indicators of how well the disease is controlled and treated. The Centers for Disease Control and Prevention has recommended that temporal and geographic specificity of COPD surveillance data be monitored to improve COPD treatment. Currently, healthcare providers are limited to a retrospective analysis of small proportions of attacks that led to emergency room visits and hospitalizations (i.e. the most severe exacerbations). These in-patient visits may indicate where the patient lives or the location of the health facility where they received treatment, but provide no precise information about when or where their exacerbation began.

Additionally, recently revised national guidelines urge doctors to more closely monitor whether prescribed treatment is controlling everyday symptoms and improving quality of life. Healthcare providers, however, are limited by an availability of tools to assess how well their patients are doing on a day-to-day basis. An increasing number of physicians have begun to use periodic, written questionnaires (e.g. the COPD Assessment Test (CAT)) to monitor patients and determine their level of control. These instruments require patients to accurately recall and report the frequency of symptoms, medicament device (e.g. inhaler) usage, and activity level and restriction over some period of time, usually two to four weeks. As a result, collected information relating to COPD management has been subject to error introduced by biases (e.g. fallible recollection), different interpretations of symptoms, and behaviors (e.g. non-adherence), and extremely limited frequency of data collection such that the data is of limited utility.

SUMMARY

A COPD analytics system is a unified platform for treating, monitoring, and managing exacerbations resulting from COPD. The COPD analytics system receives COPD rescue medication events by receiving notifications from a sensor attached to a medicament device (e.g. inhaler) used by a patient who has authorized the COPD analytics system to help manage their COPD. The sensor, when attached to or incorporated in a metered dose inhaler or other medicament device, records the geographical location, time, and date where and when a rescue medication event takes place, and communicates that information to the COPD analytics system. The COPD analytics system analyzes the received events (both the most recent and previously received events) in real time or near-real time, and delivers timely information on the use of inhaled medications to inform and guide management of the disease, including alerts to patients and the healthcare providers.

By providing timely information about the timing and frequency of the usage of the medication or medical device, and identifying the geographic location where an individual uses their medication or medical device, the COPD analytics system may help prevent COPD exacerbations by suggesting immediately applicable changes of behavior, facilitate better management of a COPD treatment by the patient and their health care provider, and improve recognition of specific locations (such as workplace, school, or home, among others) that precipitate exacerbations in order that the patient may avoid or modify these locations to prevent future exacerbations.

The COPD analytics system is also able to aggregate the received event data anonymously across multiple patients to identify temporal and geographic patterns of rescue medication events. As a result, the COPD analytics system is able to provide healthcare providers and environmental health agencies with a real-time or near-real time way to (A) identify clusters of exacerbations, (B) assess the burden of disease in a population or some portion of the population, and in some geographic area, (C) plan and evaluate public health interventions to reduce morbidity, and (D) detect new epidemiological patterns or risk factors.

DETAILED DESCRIPTION

I. System Environment

Figure 1:
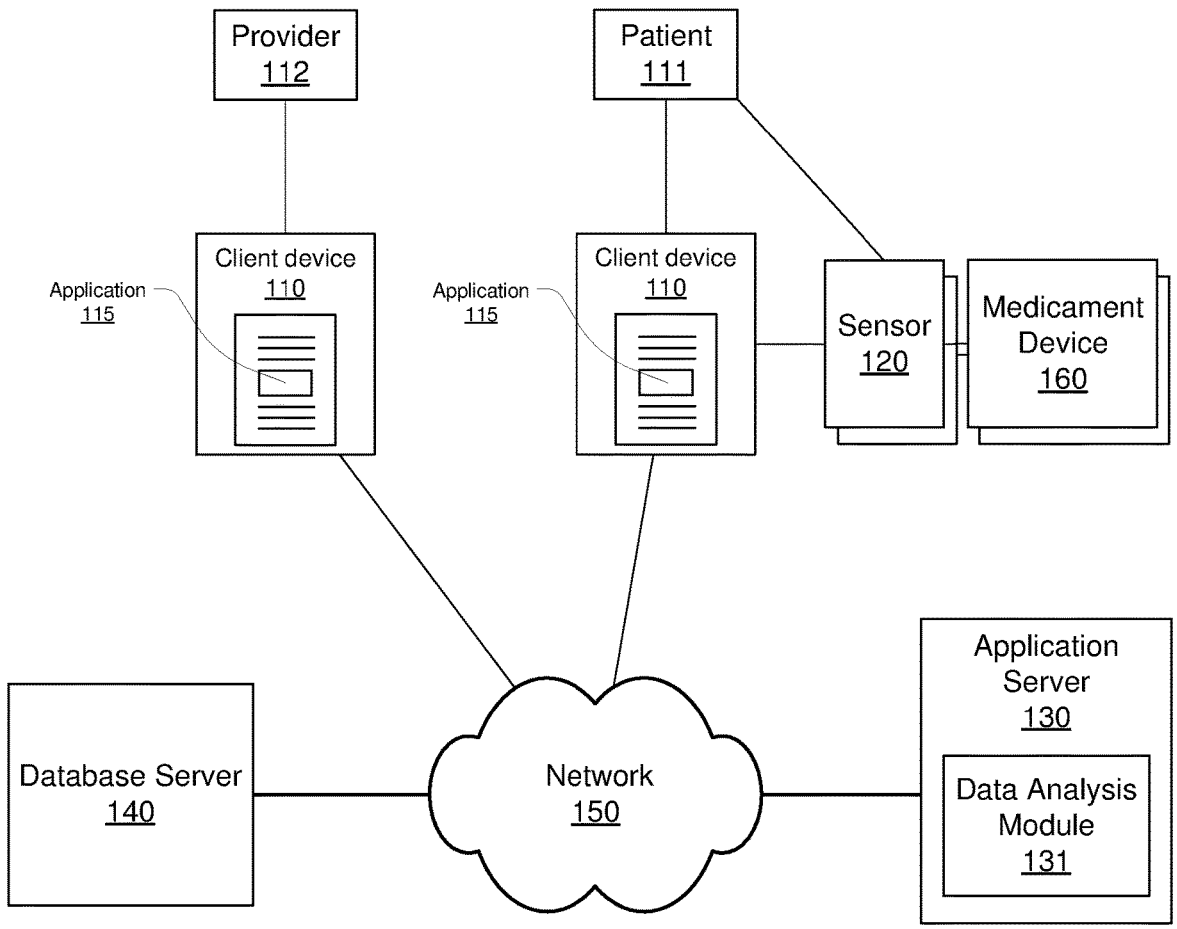
FIG. 1 shows a COPD analytics system for monitoring accurate, real-time medicament device usage, performing analytics on that data, and providing COPD exacerbation risk notifications, according to one embodiment.

FIG. 1 shows a COPD analytics system 100 for monitoring accurate, real-time medicament device events, performing analytics on that data, and providing COPD exacerbation risk notifications, according to one embodiment.

The COPD analytics system includes client computing devices 110, a medicament device sensor 120, a medicament device 160, an application server 130, database server 140, and a network 150. Although FIG. 1 illustrates only a single instance of most of the components of the COPD analytics system 100, in practice more than one of each component may be present, and additional or fewer components may be used.

I.A. Client Device and Application

The client devices 110, at the behest of their users, interact with the COPD analytics system 100 via the network 150. For purposes of explanation and clarity it is useful to identify at least two different types of users. A patient 111 is a user burdened with COPD who makes use of the COPD analytics system 100 at least in part to obtain personalized COPD exacerbation risk notifications provided by the server 130 and COPD management notifications created by their health care provider 112. Such notifications can be provided in exchange for the user's permission to allow the COPD analytics system 100 to monitor the patient's 111 medicament device 160 usage. As will be explained below, medication events are detected by a sensor 120 associated with the medicament device 160 and the user's client device 100, which in turn reports to the application server 130, which in turn can initiate a process to generate risk notifications which are provided to the user through the client device 110.

Another type of user is a healthcare provider 112 who, again with the patient's 111 express permission, also receives notifications regarding a patient's COPD management, as well as aggregated COPD community rescue event data and derived statistics regarding COPD events and other associated data. Other types of users are also contemplated, such as parents/guardians of patients 111 who may also with to receive notifications in the event that their own client devices 110 are distinct from that of their children.

The client device 110 is a computer system, an example physical implementation which is described more completely with respect to FIG. 2, below. The client device 110 is configured to wirelessly communicate with the COPD analytics system 100 via network 150. With network 150 access, the client device 110 transmits to system 100 the user's geographical location and the time of a controller or rescue medication event, as well as information describing the event as received from the associated medicament device sensor 120 (referred to throughout as "sensor 120").

Regarding user location and event times, the client device 110 may determine the geographical location and time of a rescue event through use of information about the cellular or wireless network 150 to which it is connected. For example, the current geographical location of the client device 110 may be determined by directly querying the software stack providing the network 150 connection. Alternatively, the geographical location information may be obtained by pinging an external web service (not shown in FIG. 1) made accessible via network 150. The time of an event can be provided by the sensor 120 as part of the event data or added to event data by querying an appropriate software routine available as part of the client device's native operating system.

In addition to communicating with the application server 130, client devices 110 connected wirelessly to the COPD analytics system 100 may also exchange information with other connected client devices 110. For example, through a client software application 115, a healthcare provider 112 may receive a risk exacerbation notification describing a recent rescue event about a patient 111, then in response send a recommendation to the patient 111 for post-COPD exacerbation treatment. Similarly, through application 115 patients 111 may communicate with their health care providers 112 and other patients 111.

Application 115 provides a user interface (herein referred to as a "dashboard") that is displayed on a screen of the client device 110 and allows a user to input commands to control the operation of the application 115. The dashboard is the mechanism by which healthcare providers 112 and patients 111 access the COPD analytics system 100. For example, the dashboard allows patients 111 and providers 112 to interact with each other, receive COPD exacerbation risk notifications, exchange messages about treatment, provide and receive additional event and non-event data, and so on. Application 115 may be coded as a web page, series of web pages, or content otherwise coded to render within an internet browser. Application 115 may also be coded as a proprietary application configured to operate on the native operating system of the client device 110. The dashboard is more completely described below in conjunction with FIG. 3.

In addition to providing the dashboard, application 115 may also perform some data processing on COPD rescue event data locally using the resources of client device 110 before sending the processed data through the network 150. Event data sent through the network 110 is received by the application server 130 where it is analyzed and processed for storage and retrieval in conjunction with database server 140. The application server 130 may direct retrieval and storage request to the database system 130 as required by the client application 115.

The client device 110 communicates with the sensor 120 using a network adapter and either a wired or wireless communication protocol, an example of which is the BLUETOOTH Low Energy (BTLE) protocol. BTLE is a short-ranged, low-powered, protocol standard that transmits data wirelessly over radio links in short range wireless networks. After the sensor 120 and client device 110 have been paired with each other using a BTLE passkey, the sensor 120 automatically synchronizes and communicate information relating to medicament device usage with the client device 110. If the sensor 120 hasn't been paired with a client device 110 prior to a rescue medication event, the information is stored locally until such a pairing occurs. Upon pairing, the sensor 120 communicates any stored event records to the client device 110. In other implementations, other types of wireless connections are used (e.g., infrared or 802.11).

Although client devices 110 and medicament devices 160 are described above as being separate physical devices (such as smart phones and inhalers, respectively), in the future it is contemplated the medicament devices 160 may include not only sensors 120 integrated into a single housing with the device 160, but also aspects of the client device 110. For example, a medicament device 160 may include an audio-visual interface including a display or other lighting elements as well as speakers for presenting visual audible information. In such an implementation the medicament device 160 itself may present the contents of notifications provided by the server 130 directly, in place of or in addition to presenting them through the client devices 110.

I.B. Medicament Device and Sensor

The medicament device 160 is a medical device used to deliver medication to the lungs of a user experiencing constricted respiratory airflow. Medicament devices (e.g. inhalers) are typically portable and small enough to be carried by hand for ease of accessibility when treating respiratory attacks. In one embodiment, medicine is delivered in aerosol form through a medicament device 160 such as a metered dose inhaler. Metered dose inhalers included a pressured propellant canister of aerosol medicine, a metering valve for delivering a regulated medicine dosage amount, and a plastic holder that holds the pressurized canister and also forms a mouthpiece for delivery of the medicine. In another embodiment, medicine is delivered in dry powder form through a medicament device 160 such as a dry powder inhaler. Dry powder inhalers may have Cartesian ovular shaped bodies that house wheel and gear mechanisms enabling a user to index through a strip of dry powder medication. The bodies of dry powder inhalers also include a manifold and a mouthpiece to deliver dry powder to the user. Examples of controller medications that are dispensed by a controller medicament device 160 include beclomethasone, budesonide, and fluticasone as well as combinations of those medications with a long-acting bronchodilator such as salmeterol or formoterol. Examples of rescue medications that are dispensed by a rescue medicament device 160 include albuterol, salbutamol, levalbuterol, metaproterenol, and terbutaline.

Each patient may be associated with more than one medicament device 160. For example, the patient may have a rescue medicament device 160 that dispenses rescue medication, and a controller medicament device 160 that dispenses controller medication. Similarly, each patient may be associated with more than one sensor 120, each chosen to operate with one of the patient's medicament devices 160.

Generally, a sensor 120 is a physical device that monitors the usage of the medicament dispenser 160. The sensor 120 is either removably attachable to the medicament dispenser without impeding the operation of the medication dispenser, or the sensor 120 is an integrated component that is a native part of the medicament dispenser 160 as made available by its manufacturer.

The sensor 120 includes its own network adapter (not shown) that communicates with the client device 110 either through a wired connection, or more typically through a wireless radio frequency connection. In one embodiment, the network adapter is a BLUETOOTH Low Energy (BTLE) wireless transmitter, however in other embodiments other types of wireless communication may be used (e.g., infrared, 802.11).

The sensor 120 may also be configured to communicate more directly with the application server 130. For example, if the network adapter of the sensor 120 is configured to communicate via a wireless standard such as 802.11 or LTE, the adapter may exchange data with a wireless access point such as a wireless router, which may in turn communicate with the application server 130 without necessarily involving the client device 110 in every exchange of data. These two methods of communicating are not mutually exclusive, and the sensor 120 may be configured to communicate with both the client device 110 and the application server 130, for example using redundant transmission to ensure event data arrives at the application server 130 or to provide information directly to the client device 110 while the application server 130 is determining what notification to provide in response to an event.

As introduced above, the sensor 120 captures data about usage of the medicament device 160. Specifically, each sensor 120 captures the time and geographical location of either controller or rescue medication event, that is, usages of either the controller or rescue medicament device 160, respectively, by the patient 111. Each sensor 120 transmits the event data in real-time or as soon as a network connection is achieved, automatically without input from the patient 111 or health care provider 112. The medication event information is sent to the application server 130 for use in analysis, generation of COPD exacerbation risk notifications, and in aggregate analyses of event data across multiple patients.

To accomplish this goal, there are a number of different ways for the sensor 120 to be constructed, and in part the construction will depend upon the construction of the medicament device itself 160. Generally, all sensors 120 will include an onboard processor, persistent memory, and the network adapter mentioned above that together function to record, store, and report medication event information to the client device 110 and/or server 130. Sensors 120 may also include a clock for recording the time and date of events.

Regarding specific sensor 120 constructions, traditional inhalers, such as mechanical dose counters, are not designed with sensors 120 in mind, and thus the sensor 120 may be constructed accordingly. Some implementations in this manner include mechanical, electrical, or optical sensors to detect movement of the device 160, priming of the device, activation of the device, inhalation by the user, etc. In contrast, modern inhalers, such as deflectable membrane dose counters, include electrical circuitry may report event information as an electrical data signal which a sensor 120 is designed to receive and interpret, for example the medicament device 160 itself may report movement, priming, and activation to the sensor 120.

More information regarding hardware and software components for the sensors 120 and medicament devices 160, as well as the interaction between them to record one or both of controller and rescue medication events can be found in U.S. patent application Ser. No. 12/348,424, filed Jan. 1, 2009, and International Application No. PCT/US2014/039014, filed May 21, 2014, both of which are incorporated by reference herein in their entirety.

I.C. Application Server

The application server 130 is a computer or network of computers. Although a simplified example is illustrated in FIG. 2, typically the application server will be a server class system that uses powerful processors, large memory, and faster network components compared to a typical computing system used, for example, as a client device 110. The server typically has large secondary storage, for example, using a RAID (redundant array of independent disks) array and/or by establishing a relationship with an independent content delivery network (CDN) contracted to store, exchange and transmit data such as the COPD notifications contemplated above. Additionally, the computing system includes an operating system, for example, a UNIX operating system, LINUX operating system, or a WINDOWS operating system. The operating system manages the hardware and software resources of the application server 130 and also provides various services, for example, process management, input/output of data, management of peripheral devices, and so on. The operating system provides various functions for managing files stored on a device, for example, creating a new file, moving or copying files, transferring files to a remote system, and so on.

The application server 130 includes a software architecture for supporting access and use COPD analytics system 100 by many different client devices 110 through network 150, and thus at a high level can be generally characterized as a cloud-based system. The application server 130 generally provides a platform for patients 111 and healthcare providers 112 to report data recorded by the sensors associated with their medicament devices 160 including both rescue medication and controller medication events, collaborate on COPD treatment plans, browse and obtain information relating to their condition and geographic location, and make use of a variety of other functions.

Generally, the application server 130 is designed to handle a wide variety of data. The application server 130 includes logical routines that perform a variety of functions including checking the validity of the incoming data, parsing and formatting the data if necessary, passing the processed data to a database server 140 for storage, and confirming that the database server 140 has been updated.

The application server 130 stores and manages data at least in part on a patient by patient basis. Towards this end, the application server 130 creates a patient profile for each user. The patient profile is a set of data that characterizes a patient 111 of the COPD analytics system 100. The patient profile may include identify information about the patient such as age, gender, current rescue medication, current controller medication, notification preferences, a controller medication adherence plan, and a list of non-patient users authorized to access to the patient profile. The profile may further specify a device identifier, such as a unique media access control (MAC) address identifying the one or more client devices 110 or sensors 120 authorized to submit data (such as controller and rescue medication events) for the patient.

The profile may specify which different types of notifications are provided to patients 111 and their personal healthcare providers 112, as well as the frequency with which notifications are provided. For example, a patient 111 may authorize a healthcare provider 112 to receive notifications indicating a rescue event or a change in the patient's COPD control level. The patient 111 may also authorize their healthcare provider 112 be given access to their patient profile and rescue event history. If the healthcare provider 112 is provided access to the patient profile of the patient 111, the healthcare provider may specify controller adherence or rescue medication plans. Medication plans may include a prescribed number of doses per day for controller medications.

The application server 130 also creates profiles for health care providers 112. A health care provider profile may include identifying information about the health care provider 112, such as the office location, qualifications and certifications, and so on. The health care provider profile also includes information about their patient population. The provider profile may include access to all of the profiles of that provider's patients, as well as derived data from those profiles such as aggregate demographic information, rescue and controller medication event patterns, and so on. This data may be further subdivided according to any type of data stored in the patient profiles, such as by geographic area (e.g., neighborhood, city) over by time period (e.g., weekly, monthly, yearly).

The application server 130 receives rescue medication event information from the client device 110 or the sensor 120, triggering a variety of routines on the application server 130. In the example implementation illustrated in FIGS. 4-6 below, the data analysis module 131 executes routines to access COPD event data as well as other data including a patient's profile, analyze the data, and output the results of its analysis to both patients 111 and providers 112. This process is generally referred to as a COPD risk analysis.

The COPD risk analysis itself may include several different analyses. The exact analyses performed at any point in time or in response to any given rescue or controller medication event may vary either by implementation, and/or based on the received event data, the particular data already present in the patient's profile, or in response to changes in the COPD risk score in patient profiles connected directly to the patient's profile or indirectly through a common health care provider. For example, several patients connected to a health provider may experience rescue or controller medication events triggering a COPD risk analysis on a patient's profile that may not have any recent medication events. One such analysis determines the risk of a patient having an acute COPD exacerbation based on controller and rescue medication event data captured over several different sliding time windows extending back from the present. Generally, an acute exacerbation of COPD, also known as acute exacerbations of chronic bronchitis (AECB), is a sudden worsening of COPD symptoms (shortness of breath, quantity and color of phlegm) that typically lasts for several days.

Other analyses are also possible. For example, a risk analysis may be performed on rescue and controller medication use for multiple patients to identify based on spatial/temporal clusters (or outbreaks) of medication use based on historically significant permutations from individual, geographic, clinical, epidemiologic, demographic, or spatial or temporal baselines or predicted or expected values. Other types of analyses include daily/weekly adherence trends, adherence changes over time, adherence comparisons to other relevant populations (e.g., all patients, patients on a particular rescue medication or controller medication or combination thereof, identification of triggers (spatial, temporal, environmental), rescue use trends over time, and rescue use comparisons to other relevant populations.

Responsive to any analyses performed, the application server 130 prepares and delivers push notifications to send to patients 111, authorized healthcare providers 112, and/or other users provided access to the patient's profile. Notifications can provide details about the timing, location, and affected patient(s) 111 involved in a medication rescue event. Notifications may additionally comprise a distress or emergency signal that requests emergency assistance that are distributed to emergency assistance providers 112. Notifications may also include the results of the COPD risk analysis performed by the data analysis module 131.

In addition to providing push notifications in response to a COPD risk analysis, notifications may also be provided as pull notifications, at particular time intervals. Additionally, some notifications (whether push or pull) may be triggered not in response to a COPD risk analysis performed in response to a rescue medication event, but instead in response to one of the underlying factors in the COPD risk analysis changing, such that an updated COPD risk analysis and subsequent notification is warranted. For example, if weather conditions indicate that an increase in air pollution is occurring or is imminent, this may trigger the carrying out of COPD risk analyses for all patients located in the particular geographic area where the pollution is occurring.

Notifications are provided through the network 150 to client applications 115 in a data format specifically designed for use with the client applications, and additionally or alternatively may be provided as short message service (SMS) messages, emails, phone calls, or in other data formats communicated using other communication mediums.

I.D. Database Server

The database server 140 stores data patient and provider data related data such as profiles, medication events, patient medical history (e.g., electronic medical records). Patient and provider data is encrypted for security and is at least password protected and otherwise secured to meet all Health Insurance Portability and Accountability Act (HIPAA) requirements. Any analyses (e.g., COPD risk analyses) that incorporate data from multiple patients (e.g., aggregate rescue medication event data) and are provided to users is de-identified so that personally identifying information is removed to protect patient privacy.

The database server 140 also stores non-patient data used in COPD risk analyses. This data includes regional data about a number of geographic regions such as public spaces in residential or commercial zones where patients are physically located and may be exposed to pollutants. This data may specifically include or be processed to obtain a patient's proximity to green space (areas including concentrated numbers of trees and plants) and proximity to different types of human organizations such as may be used to infer a patient's socioeconomic status. One example of regional data includes georeferenced weather data, such as temperature, wind patterns, humidity, the air quality index, and so on. Another example is georeferenced pollution data, including particulate counts for various pollutants at an instance of time or measured empirically. The regional data includes information about the current weather conditions for the time and place of the rescue event such as temperature, humidity, air quality index. All of the items of data above may vary over time, and as such the data itself may be indexed by time, for example separate data points may be available by time of day (including by minute or hour), or over longer periods such as by day, week, month, or season.

Although the database server 140 is illustrated in FIG. 1 as being an entity separate from the application server 130 the database server 140 may alternatively be a hardware component that is part of another server such as server 130, such that the database server 140 is implemented as one or more persistent storage devices, with the software application layer for interfacing with the stored data in the database is a part of that other server 130.

The database server 140 stores data according to defined database schemas. Typically, data storage schemas across different data sources vary significantly even when storing the same type of data including cloud application event logs and log metrics, due to implementation differences in the underlying database structure. The database server 140 may also store different types of data such as structured data, unstructured data, or semi-structured data. Data in the database server 140 may be associated with users, groups of users, and/or entities. The database server 140 provides support for database queries in a query language (e.g., SQL for relational databases, JSON NoSQL databases, etc.) for specifying instructions to manage database objects represented by the database server 140, read information from the database server 140, or write to the database server 140.

I.E. Network

The network 150 represents the various wired and wireless communication pathways between the client 110 devices, the sensor 120, the application server 130, and the database server 140. Network 150 uses standard Internet communications technologies and/or protocols. Thus, the network 150 can include links using technologies such as Ethernet, IEEE 802.11, integrated services digital network (ISDN), asynchronous transfer mode (ATM), etc. Similarly, the networking protocols used on the network 150 can include the transmission control protocol/Internet protocol (TCP/IP), the hypertext transport protocol (HTTP), the simple mail transfer protocol (SMTP), the file transfer protocol (FTP), etc. The data exchanged over the network 150 can be represented using technologies and/or formats including the hypertext markup language (HTML), the extensible markup language (XML), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

II. Example Computing Devices

Figure 2:
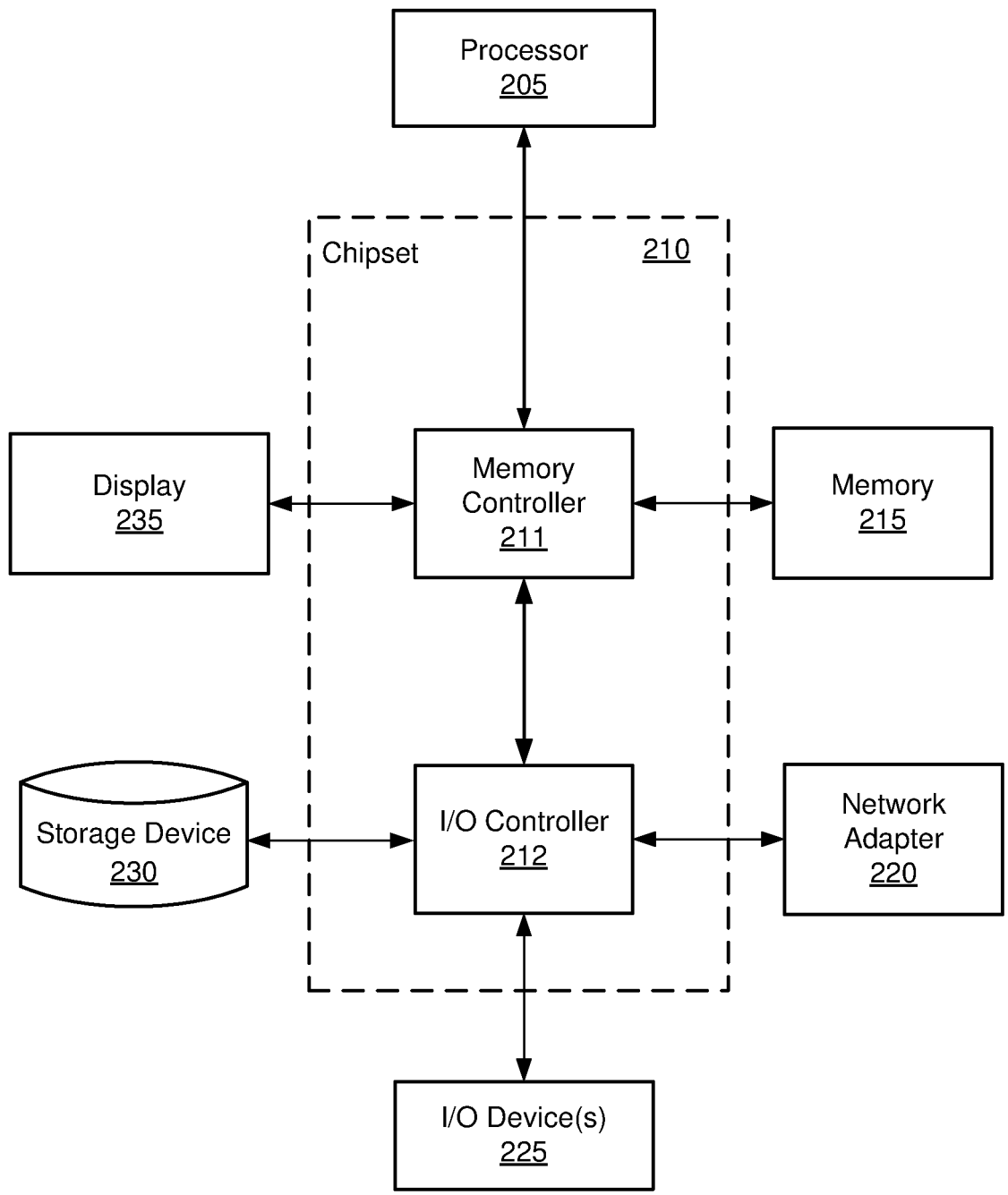
FIG. 2 is a high-level block diagram illustrating an example of a computing device used in either as a client device, application server, and/or database server, according to one embodiment.

FIG. 2 is a high-level block diagram illustrating physical components of an example computer 200 that may be used as part of a client device 110, application server 130, and/or database server 140 from FIG. 1, according to one embodiment. Illustrated is a chipset 210 coupled to at least one processor 205. Coupled to the chipset 210 is volatile memory 215, a network adapter 220, an input/output (I/O) device(s) 225, a storage device 230 representing a non-volatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive, compact disk read-only memory (CD-ROM), DVD, or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information from for the computer 200. The network adapter 220 couples the computer 200 to the network 150.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)), and, in one embodiment, the storage device 230 is not a CD-ROM device or a DVD device.

Generally, the exact physical components used in a client device 110 will vary in size, power requirements, and performance from those used in the application server 130 and the database server 140. For example, client devices 110, which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the COPD risk analyses introduced above. In one embodiment, the processing power of the application server 130 provided by a service such as Amazon Web Services™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

III. Dashboard

Figure 3A:
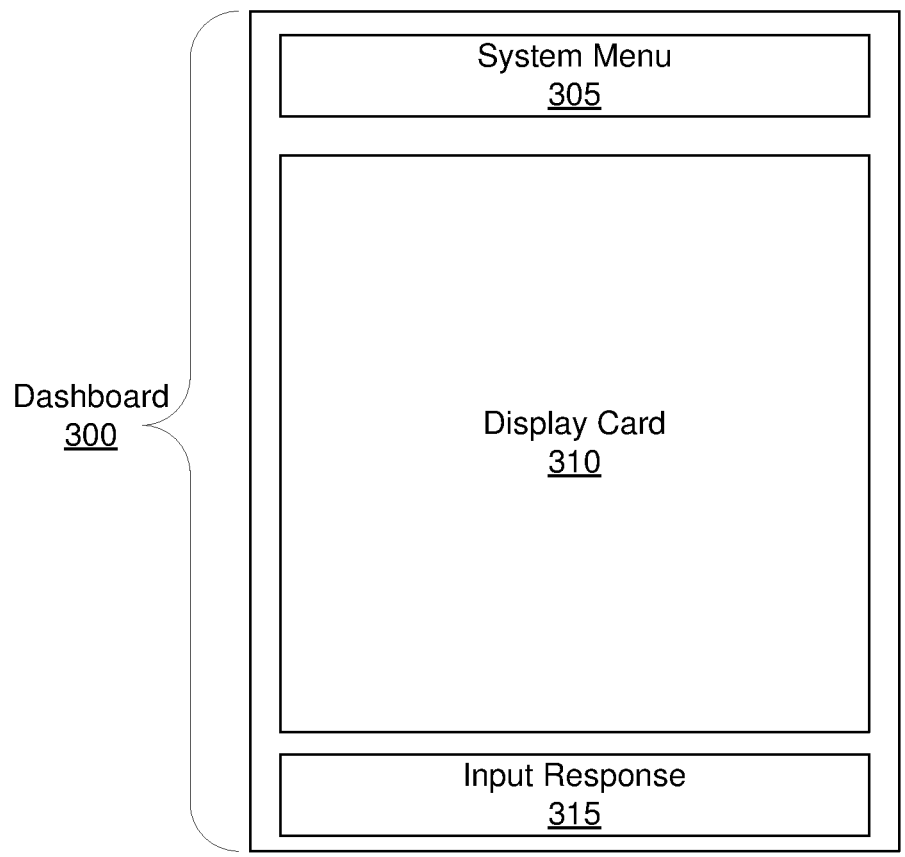
FIG. 3A shows a dashboard of a client application that allows a user to interact with a COPD analytics system, according to one embodiment.

The dashboard, for example dashboard 300 illustrated in FIG. 3A, allows users to interact with the COPD analytics system 100. The dashboard 300 provides a means to transfer information on a user-to-user (e.g., patient 111 to provider 112) or user-to-system/system-to-user basis. Dashboards 300 are accessed through the client application 115 on the client device 110 and provide a mechanism for both patients and healthcare providers to monitor medication rescue events, exchange personalized patient healthcare information, and receive notifications such as COPD exacerbation risk notifications. Patients may communicate with other health care provider and other patients through the dashboard 300, for example, to discuss and share information about COPD, medication usage, or COPD management. The ability to share COPD healthcare information may give patients or healthcare care providers experiencing a same issue a way to share individual perspectives.

The dashboard 300 also allows authorized health care providers 112 to access a list of patients to view, annotate, update, interact with, and export information about COPD patient and community data and statistics in various demographics or geographic segments. Using the dashboard 300, healthcare providers are able to monitor patients individually or in aggregate, to receive and provide feedback (e.g. compliance reminders) on how their associated patient populations are responding to COPD management guidance. A healthcare provider who has access to individual or multiple patients has the ability to establish notification thresholds, set parameters for the notifications, and receive notifications when patients' event history matches certain conditions (e.g. rescue event). Additionally, the dashboard 300 can receive and display regular reports of event patterns for specific demographic generated by the COPD analytics system 100.

The dashboard 300 presents a variety of information including tabular data, graphical visualizations, and analyses to users through display "cards" 310. Display cards 310 are conformably suited to smaller displays typical of portable client devices 110, for example mobile phones or tablets, and include "bite size" pieces of information that mimic the simplistic organizational style found in baseball cards. The dashboard 300 may also include a system menu 305 that allows users to navigate through different categories of healthcare information.

Notifications provided by the application server 130 are related to the display cards 310. Generally, notifications include not only information to be presented to the user through the application 115, but also parameters for specifying which display card 310 is to be used to display the contents of the notification. Generally, any information pushed/pulled from the application server 130 may be associated with one or more cards. For example, a notification can be pushed to the patient based on the outcome of a COPD risk analysis. The dashboard 300 will process the notification and determine which card/s to use to present the information in the notification. Continuing the example, the recipient of the notification may make a request (pull) data from the application server 130. The application server 130 provides the requested data in another notification, and the dashboard 300 then determines which display card 310 to display the requested information.

To interact with information presented, some display cards 310a include a input response 315 area. For example, in the display card 310b illustrated in FIG. 3B, a patient may scroll up or down in the input response 315 area to select a controller medication used to manage COPD or select the "next" to move to an additional display card 310.

The dashboard 300 may provide a variety of different display cards 310, which may be organized into categories. An information card type includes cards that display data. Information cards may, for example, display medication rescue events, statistics, and maps including both patient data and community data. Information cards are further sub-categorized into event trend, education, and alert display cards.

Figure 3B:
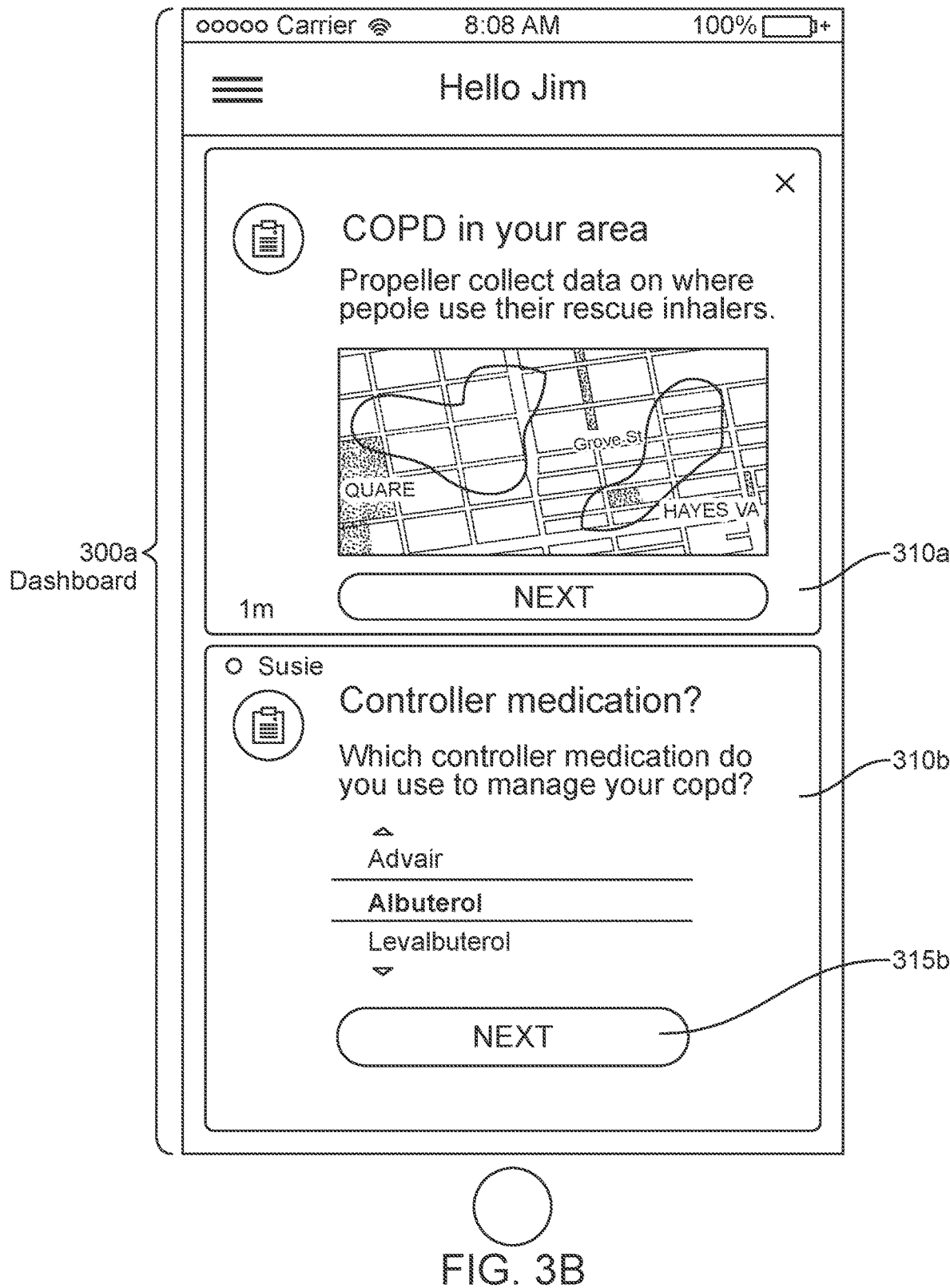
FIGS. 3B-3R illustrate example cards displayed within the dashboard of the client application, according to one embodiment.
Figure 3C:
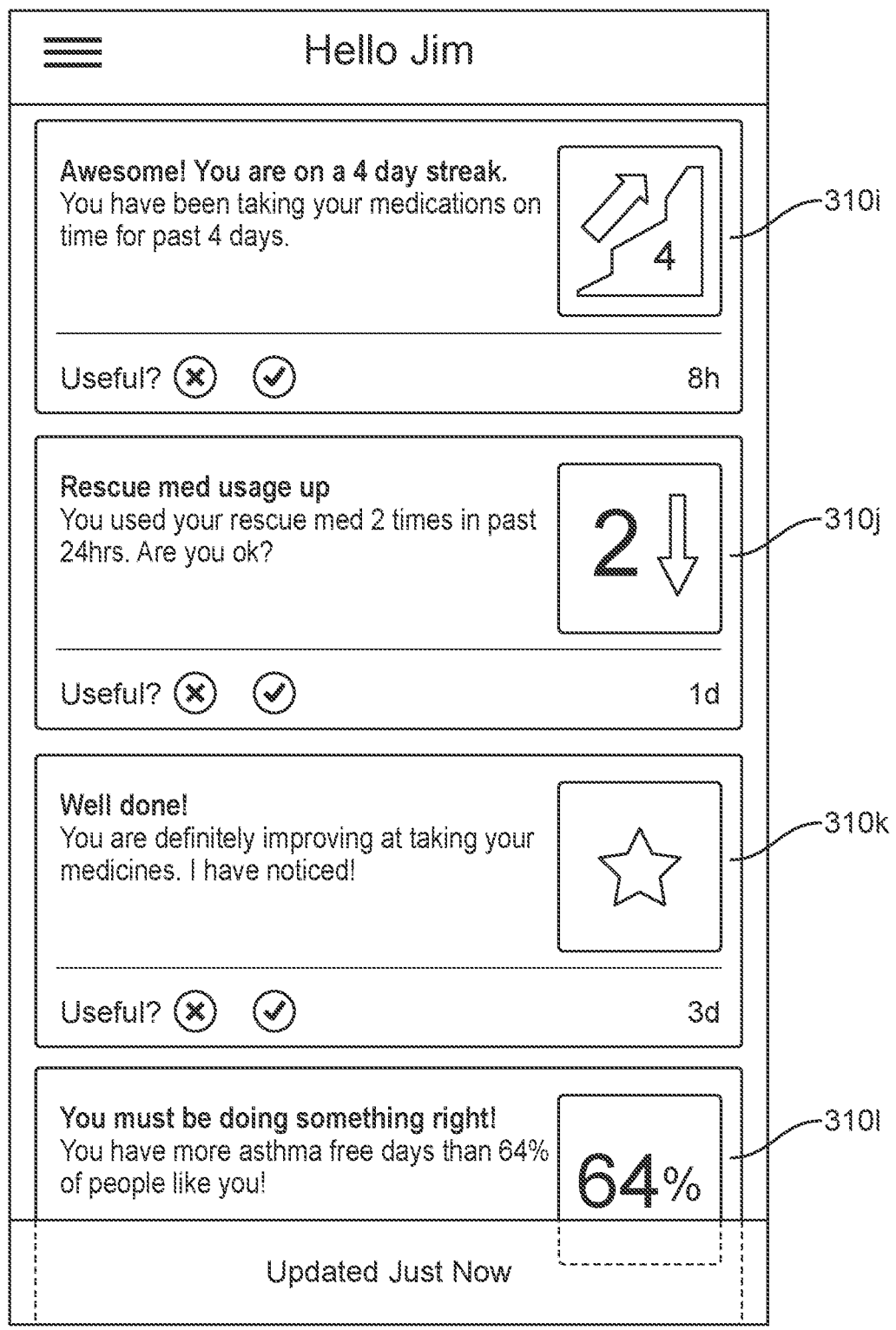
Figure 3D:
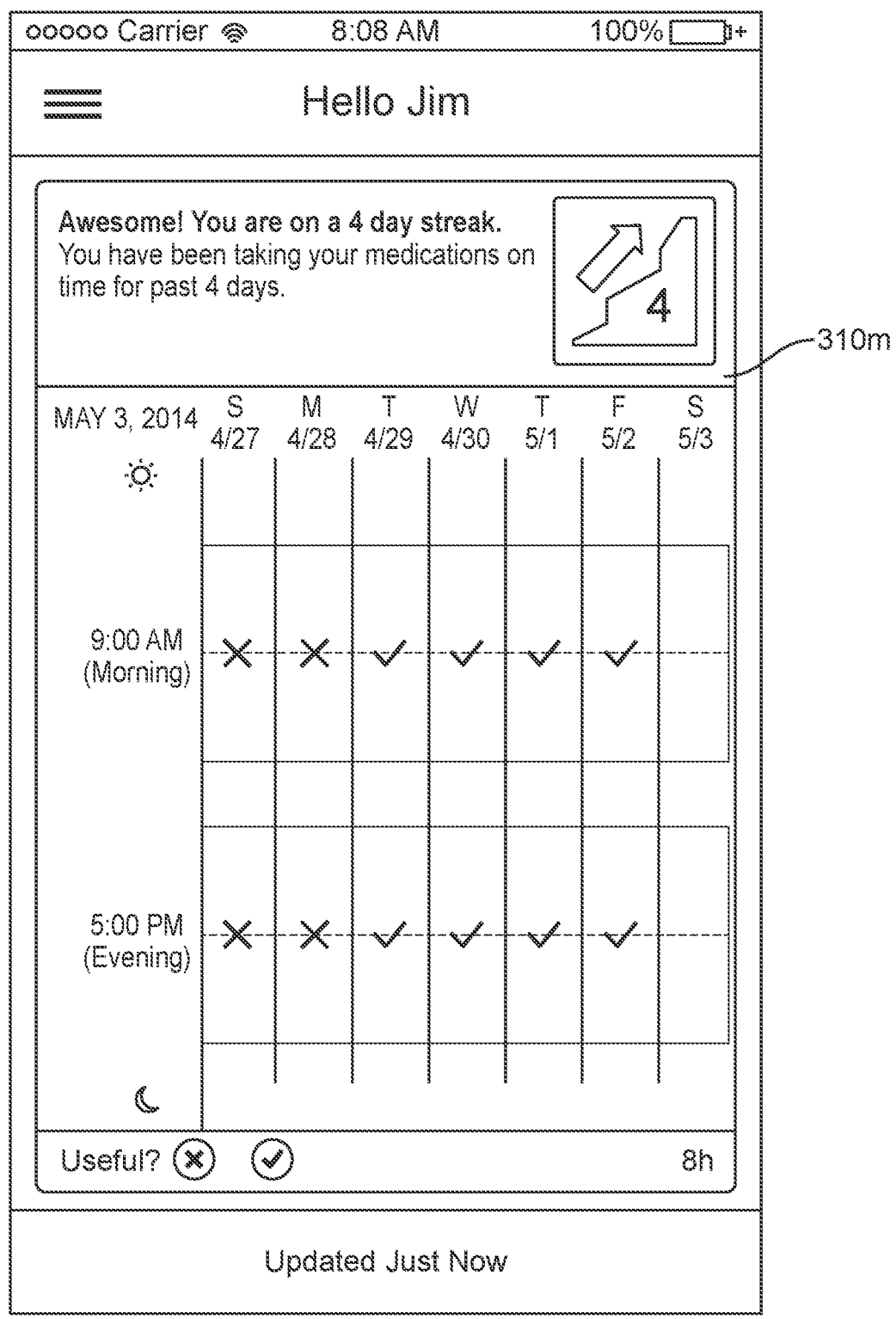
Figure 3E:
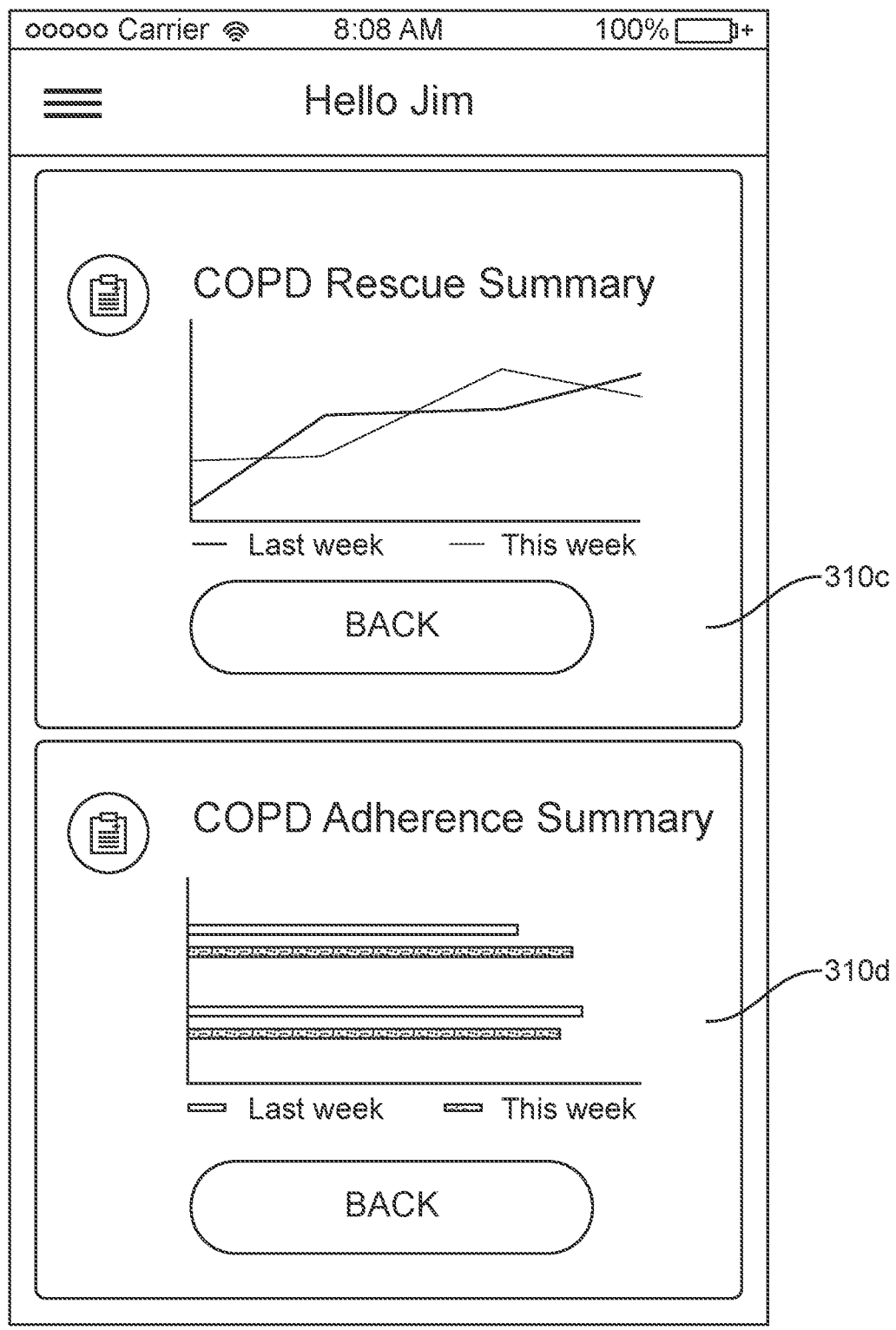
Figure 3F:
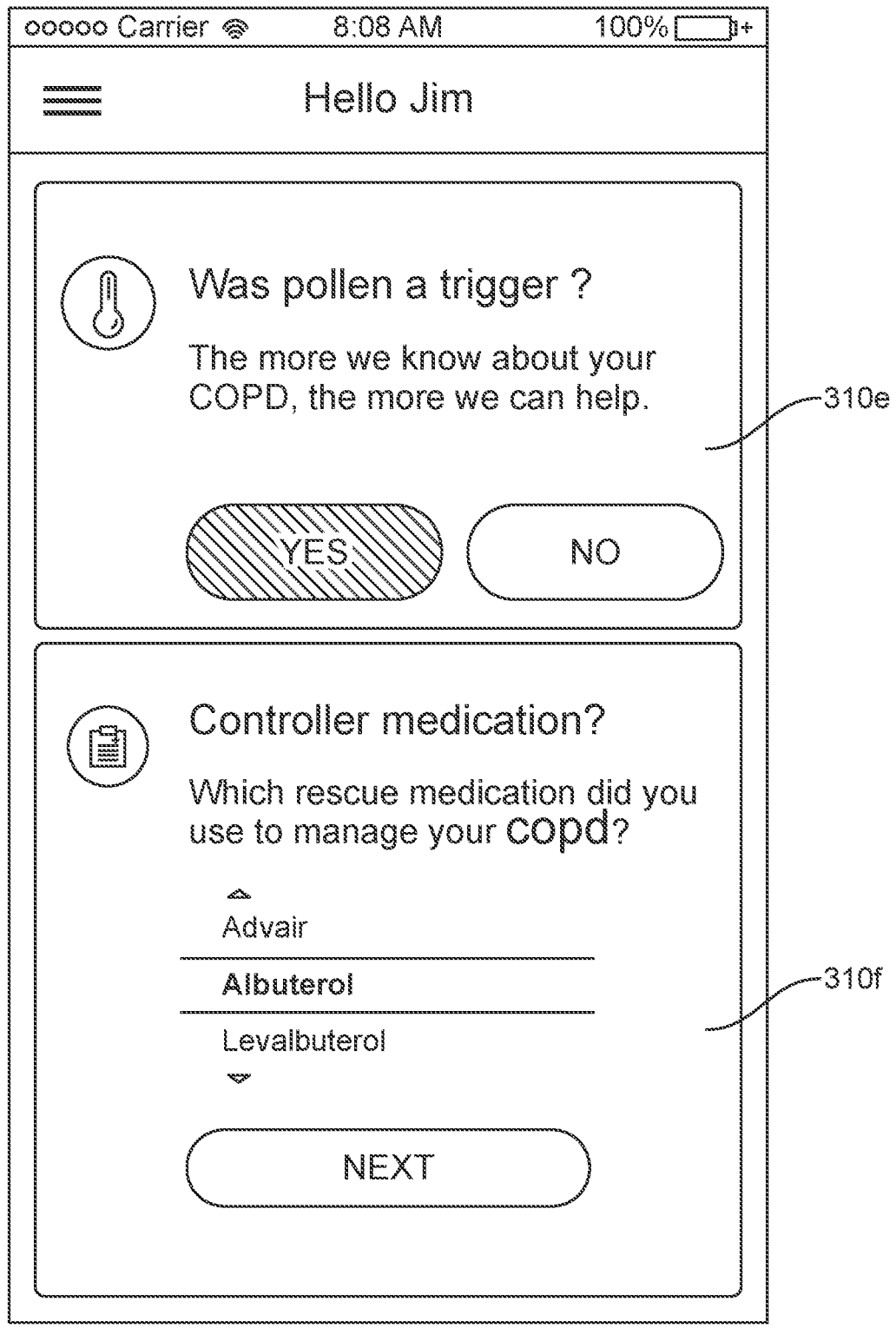
Figure 3G:
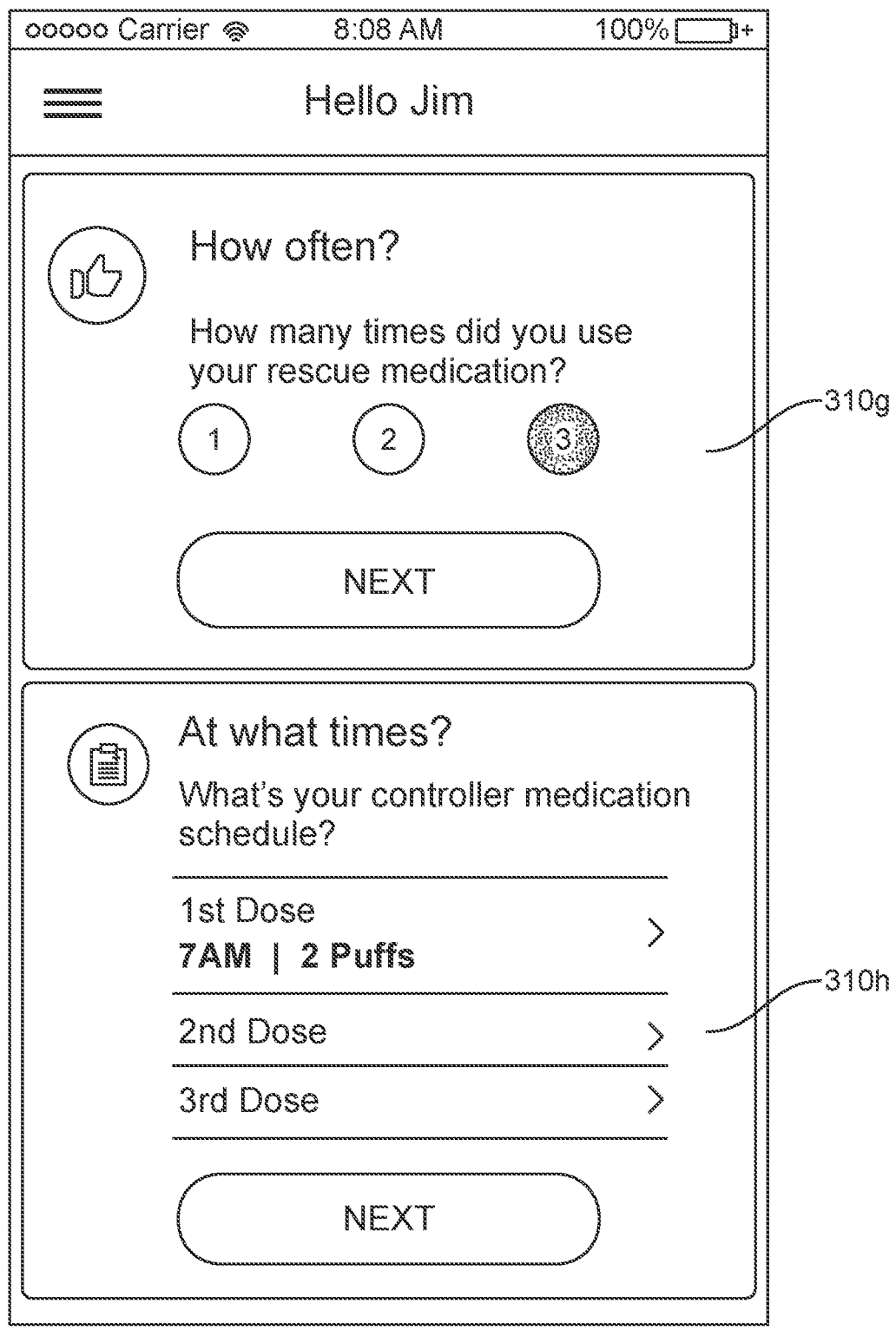
Figure 3H:
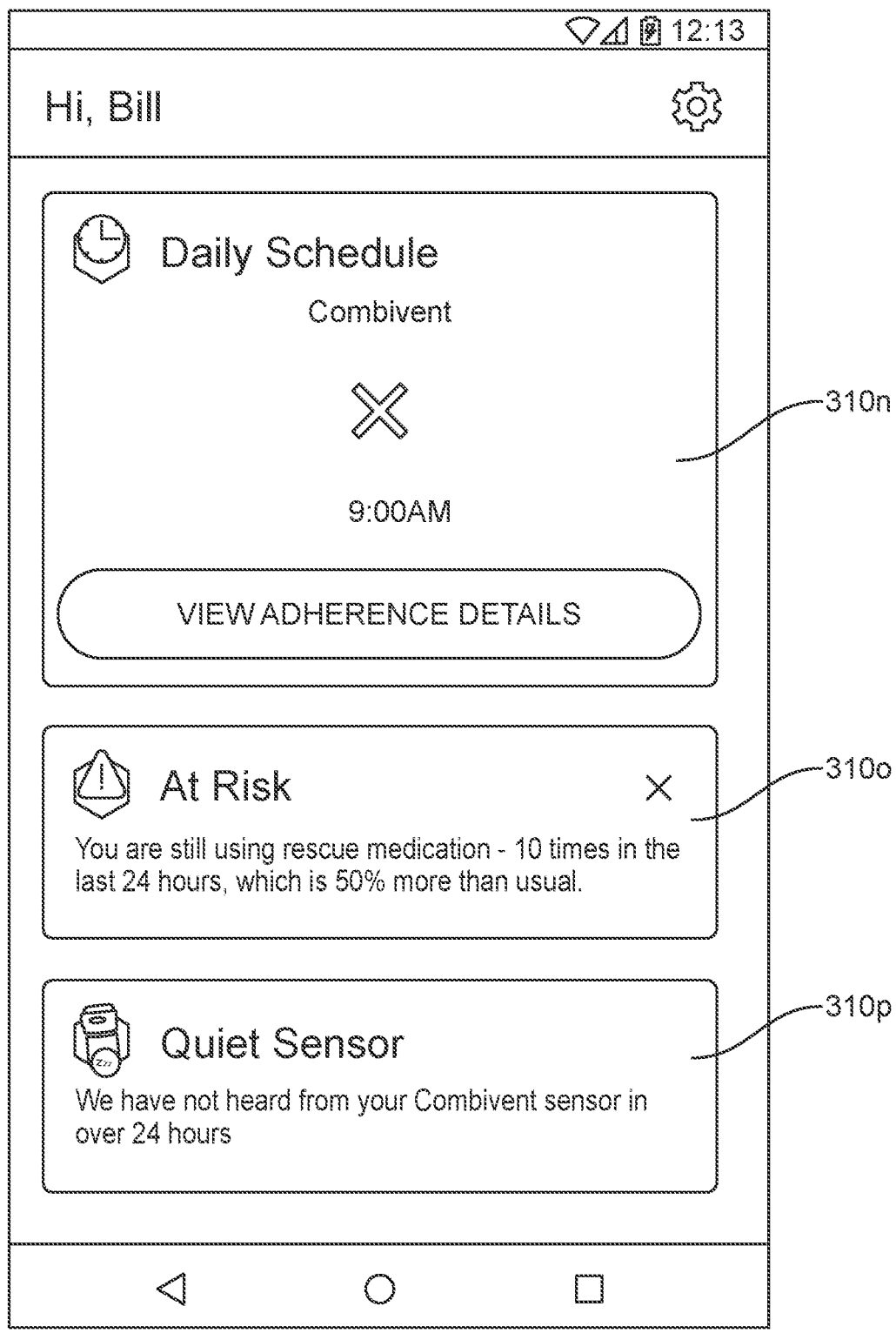
Figure 3I:
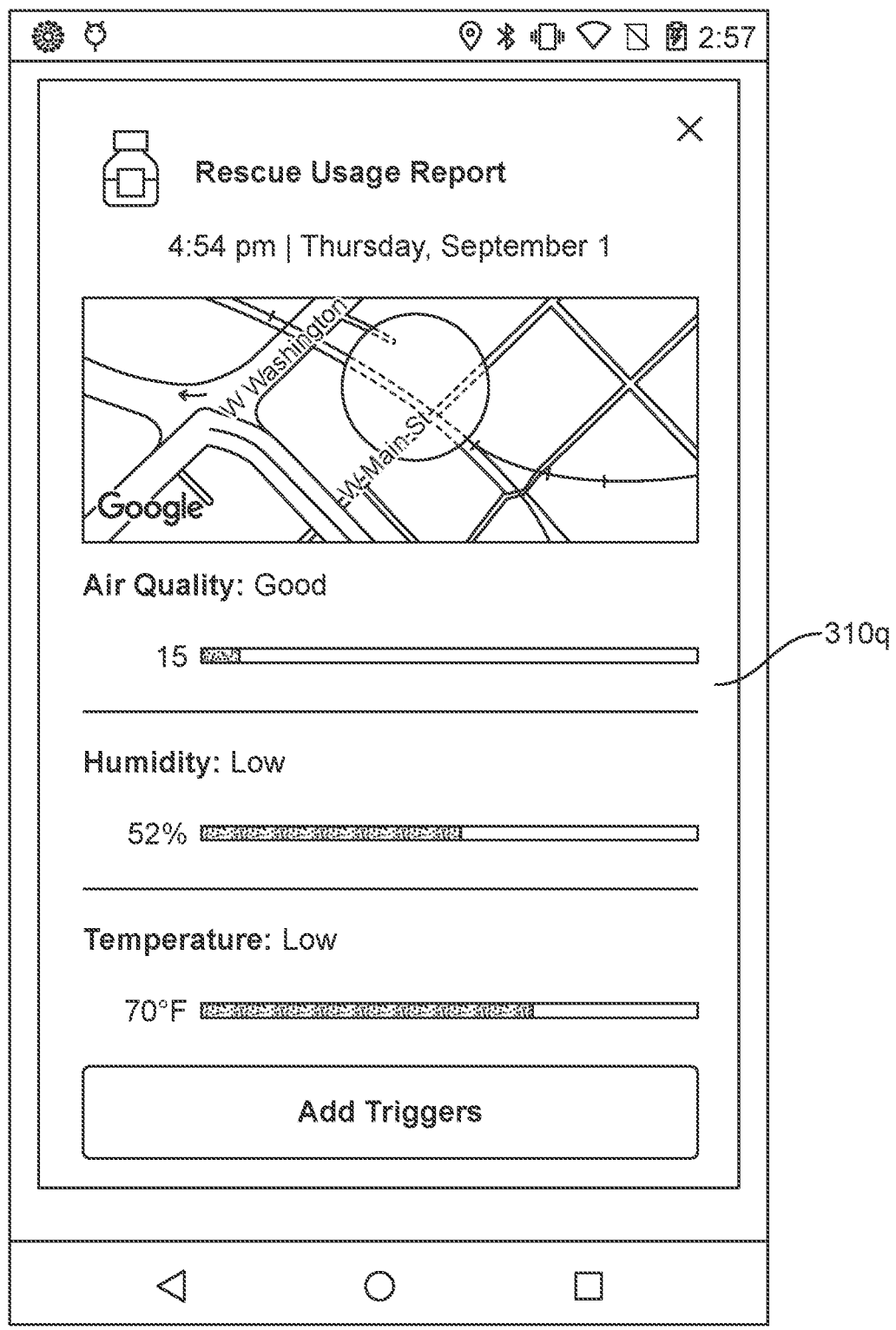
Figure 3J:
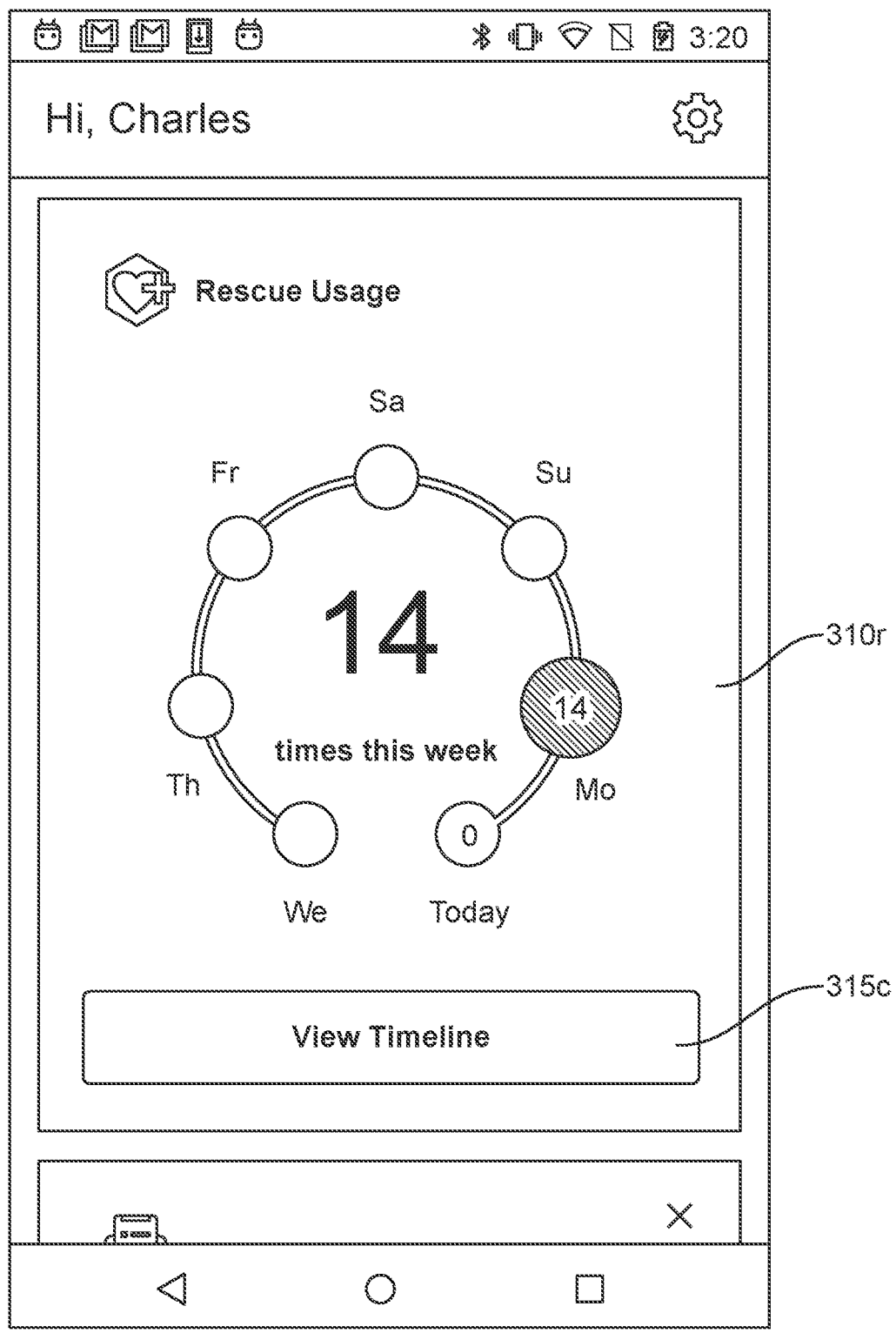

Event cards include data relating to rescue medication events, such as a list of historical medication rescue events for a specific patient, or patient rescue event data overlaid on a geographical map for a specific provider. For example, the display card 310a illustrated in FIG. 3B is an event card that highlights patients experiencing COPD rescue events in a particular geographic area. The display card 310q illustrated in FIG. 3I is an event card that displays an example medication usage report. The example medication usage report includes a map of location of a rescue usage event, environmental conditions at the location, and an input response area 315 for the recipient to add triggers for the rescue usage event. Card 310r illustrated in FIG. 3J displays rescue device usage for the previous week. The card displays a total number of uses (14) and a number of uses for each day (14 for Monday and no usage for each other day).

A trend card includes statistical information presented using a graph or a chart designed for clear comprehension by the recipient. FIG. 3E illustrates two different example trend cards, plotting COPD rescue events 310c and COPD controller medication adherence 310d, both over various time periods. FIG. 3Q illustrates four different example trend cards. Card 310aa displays a time of day trend, card 310bb displays a symptom trend, card 310cc displays a day of week trend, and card 310dd displays a trigger trend.

An education card includes information meant to educate the recipient. FIGS. 3O and 3P illustrate education cards, providing general disease information 310w and 310x and providing tips for recipients 310y and 310z. Education cards may include an input response 315 to allow recipients to specify whether the information provided is relevant or interesting for use in serving future cards.

Alert cards notify users of important information. Cards 310*o* and 310*p* of FIG. 3H are alert cards for informing a recipient that they are at risk for an event 310*o* and that data has not been received from a device over a recent time period 310*p*. FIG. 3R illustrates example alert cards. Card 310*ee* is similar to card 310*o* and card 310*ff* is similar to card 310*p*. Card 310*gg* informs a recipient that a particular dose of medication has not been recorded by a device. Other alerts may include an alert that a setting on the client device is preventing syncing (e.g., BLUETOOTH is turned off) or that a patient's Asthma Control Test score has changed.

A survey card type solicits a user response by presenting yes/no, multiple choice, or more open-ended questions for the user to respond to. For example, a healthcare provider or the COPD analytics system 100 may send a survey card with a COPD questionnaire to a patient 111 to determine a level of disease control for a specific patient. As an additional example, a survey card may request the type of controller medication that the patient 111 uses to treat COPD symptoms, as shown in the display card 310*b* illustrated in FIG. 3B. Generally, survey cards provide the application server 130 with data that may be missing from a patient's medical history or patient profile (as introduced above), and/or provide an update to possible outdated information. Generally, one or more survey cards may be used to complete the patient enrollment process and create a patient profile for storage in database server 140. As a specific example, when a patient 111 initially enrolls in the COPD analytics system 100, a push notification will be triggered by the application server 130 prompting the patient 111 to create a patient profile. Example of survey cards are illustrated in FIGS. 3F and 3G, which illustrates a survey question asking whether a patient has made an emergency room visits as a result of COPD exacerbations, what the patient's controller medication is 310*f*, how many times the patient used their rescue medication to control an event 310*g*, and what their controller medication daily schedule is 310*h*. Survey cards may also ask about a patients asthma triggers, such as whether pollen is a trigger 310*e*. Other survey cards ask a patient to rate their general quality of life on 5-point Likert scale, to rate their quality of sleep, to rate their ability to be active over last 7 days, and so on. Other survey cards ask whether the patient feels better or worse than yesterday, whether the patient has had to go to emergency room or hospital in last 12 months for an exacerbation and so on.

In some instances, patient behavior or sensor-reported event information that is inconsistent with existing patient information may trigger the sending of a survey card in order to resolve ambiguity as to the patient's circumstances. For example, if the patient is experiencing a greater-than-expected count of COPD events, the survey card may request information about the type of medication the patient is currently using as listed on their medicament device 160, in order to verify that the correct medication is being used. As another example, if the reported information about controller medication use indicates that the patient is only using the controller medication one time per day but their adherence plan indicates they are supposed to be taking their controller medication twice per day, system 100 could send a notification asking if the patient needs to change their adherence plan.

Navigation cards represent actionable data or messages that, upon user interaction, may redirect the user to another screen or card that is part of the dashboard 300. For example, if a patient wants to share information or request specific medication plans for controller medications with a physician, a navigation card would be used to facilitate the sharing of information or enrollment in controller adherence plan. Additionally, navigation cards allow users to update information surrounding medication rescue events.

Adherence cards are designed to encourage a patient to continually use their controller medication on schedule over different periods of time. FIGS. 3C, 3D, and 3H illustrate example adherence cards. Cards 310*i* illustrates an example of a "streak" or continuous run of on-time controller medication events, card 310*k* illustrates better performance in aggregate even if no streak has been achieved, and card 310*l* presents improved patient health with respect to the number of asthma or COPD symptom-free days experienced. Card 310*j* is a survey card that inquires as to the patient's physical state in response to recording a significant number (e.g., two) rescue medication events within a threshold period of time of each other (e.g., 24 hours). Card 310*m* illustrates controller medication events as a graph, illustrating when the patient 111 did and did not take their controller medication on time during various periods during the day, as prescribed by their health care provider 112. Card 310*n* illustrates a daily schedule for controller medication and an indicator for displaying whether the scheduled dose has been taken. In the example of card 310*n*, the indicator is a red "X" indicating the scheduled dose has not been taken. A green check mark or another symbol could be used to indicate that the scheduled does has been taken.

Setup cards guide recipients in associating sensors with client devices 110. FIG. 3N illustrates example setup cards for pairing a sensor to a client device 110 using BLUETOOTH. Card 310*s* prompts the recipient to initiate the pairing process. Card 310*t* prompts the user to select a sensor device for pairing. Cards 310*u* and 310*v* notify the user that the sensor is paired.

Figure 3K:
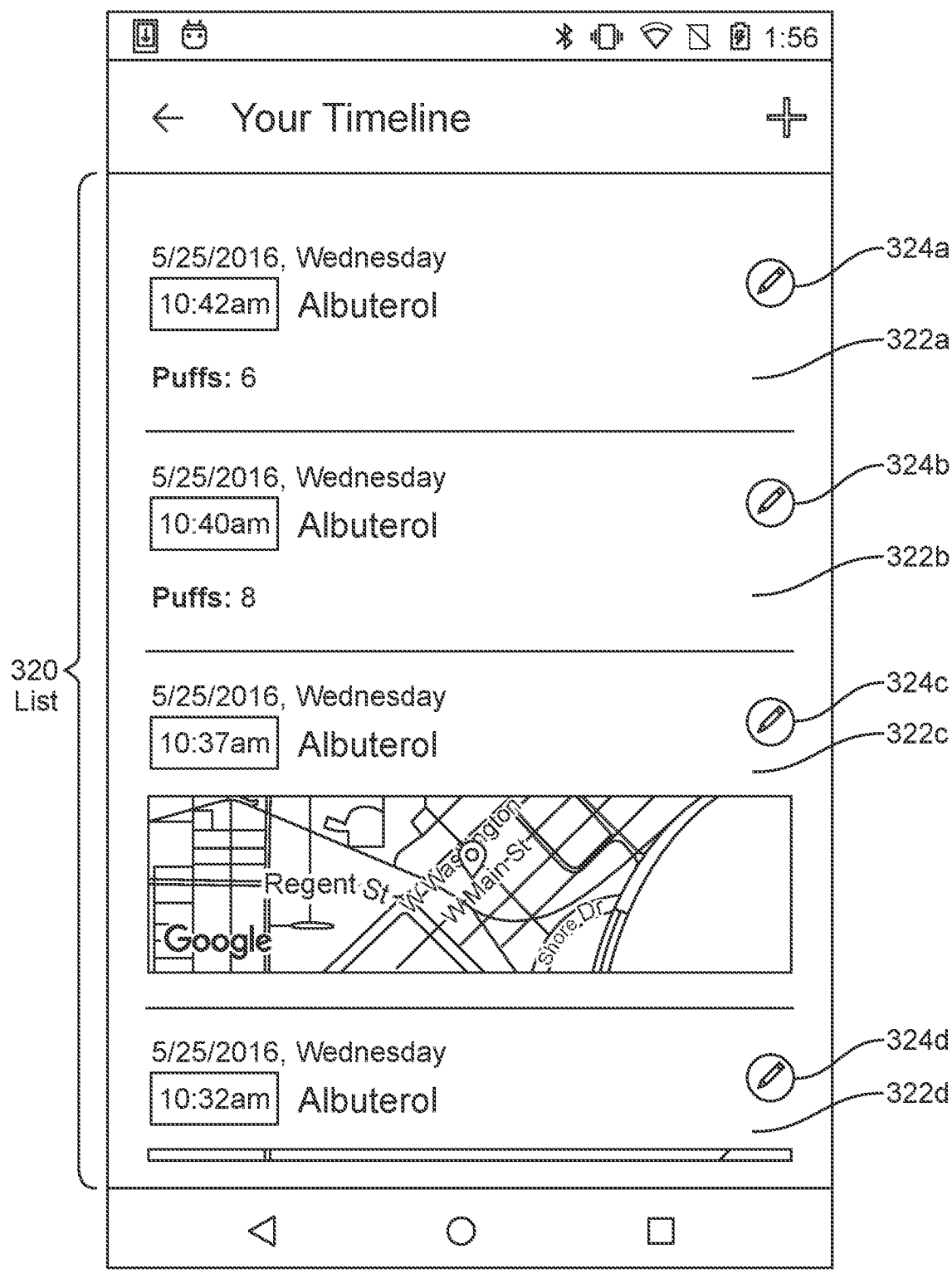
Figure 3L:
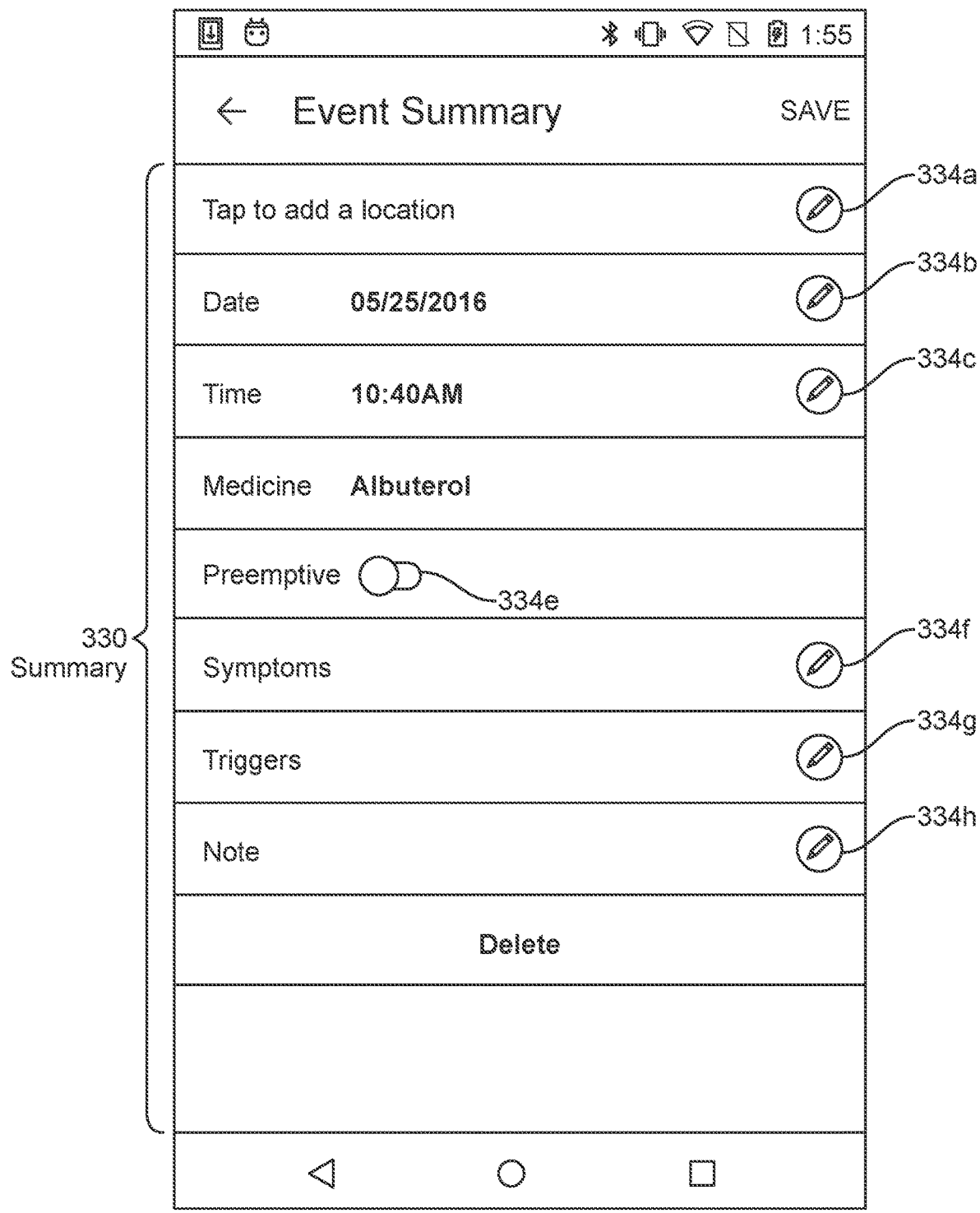
Figure 3M:
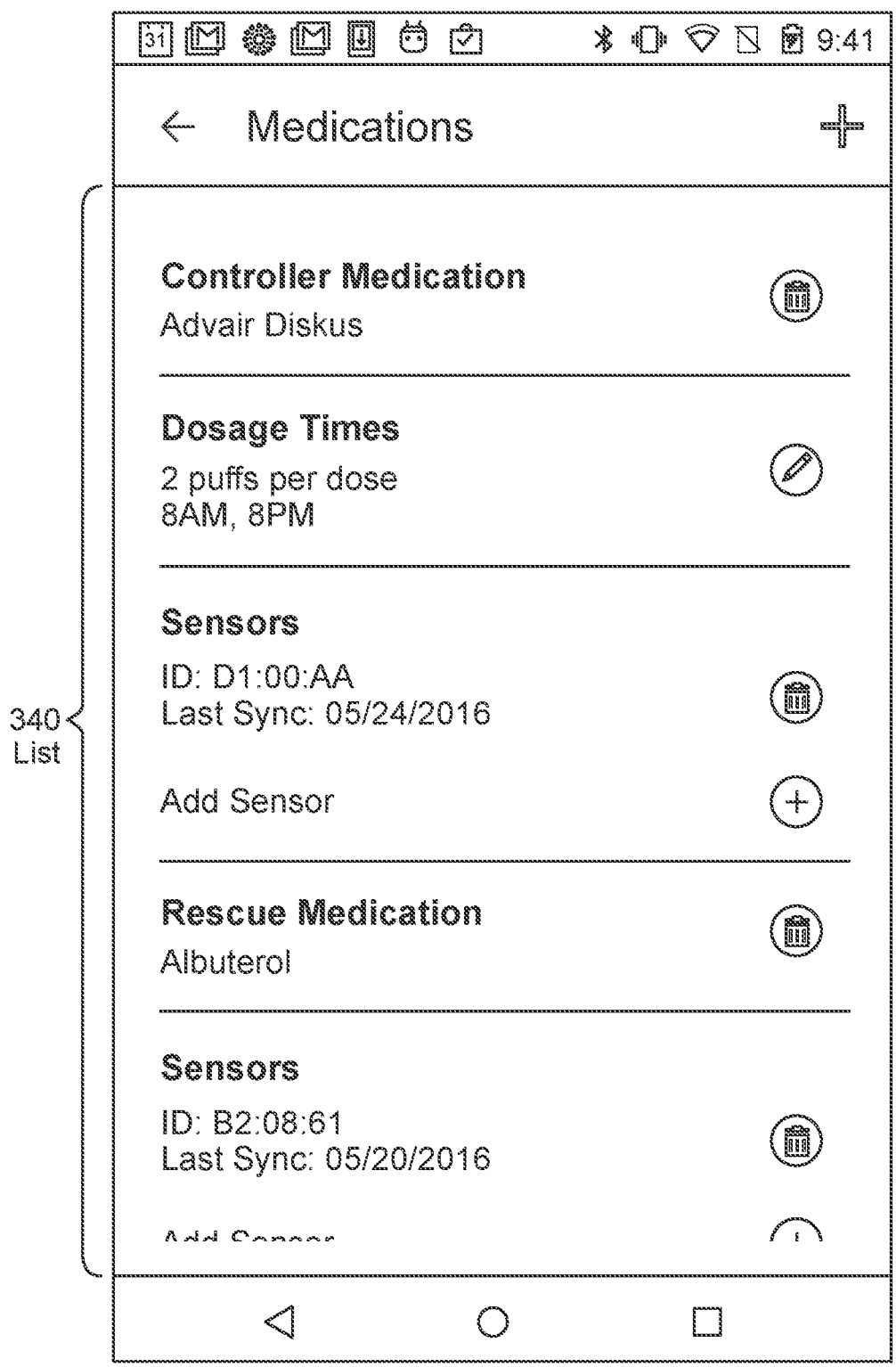
Figure 3N:
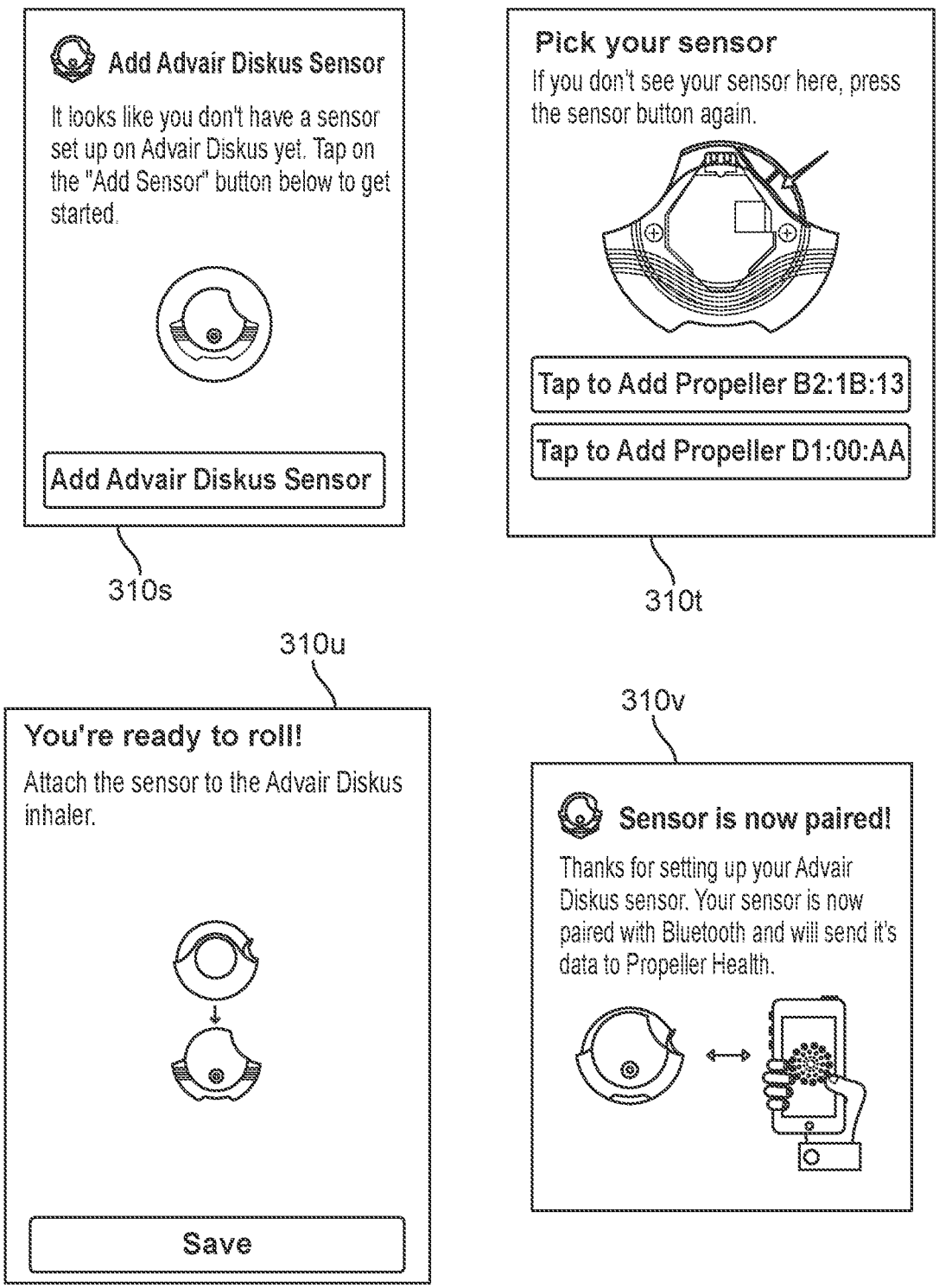

FIGS. 3K, 3L, and 3M illustrate example user interfaces presented in the dashboard 300. FIG. 3K illustrates a list 320 of rescue usage events 322*a*-322*d*. The list 320 may be presented to a recipient responsive to selection of the "View Timeline" input response area 315*c* of FIG. 3J. Returning to FIG. 3K, the list 320 displays rescue usage events over a time period and includes details such as date, time, number of puffs, and location. Recipients may edit rescue usage events and/or add additional details by selecting the edit interaction response areas 324*a-d*. FIG. 3L illustrates an example event summary 330 for a rescue usage event. The event summary 330 may be provided responsive to a user selecting the edit interaction response areas 324 of FIG. 3K. Returning to FIG. 3L, The event summary 330 provides further details regarding a rescue usage event. Recipients may edit the detail fields of the event summary 330 by selecting the interaction response areas 334*a-h* corresponding to each field. FIG. 3M illustrates a medication list 340. The list 340 includes medication information such as medication type (rescue, controller, etc.), dosage schedule, and sensors. Recipients may interact with the list 340 to add, edit, and delete medications and medication information.

IV. Event-Driven COPD Risk Notifications

Figure 4:
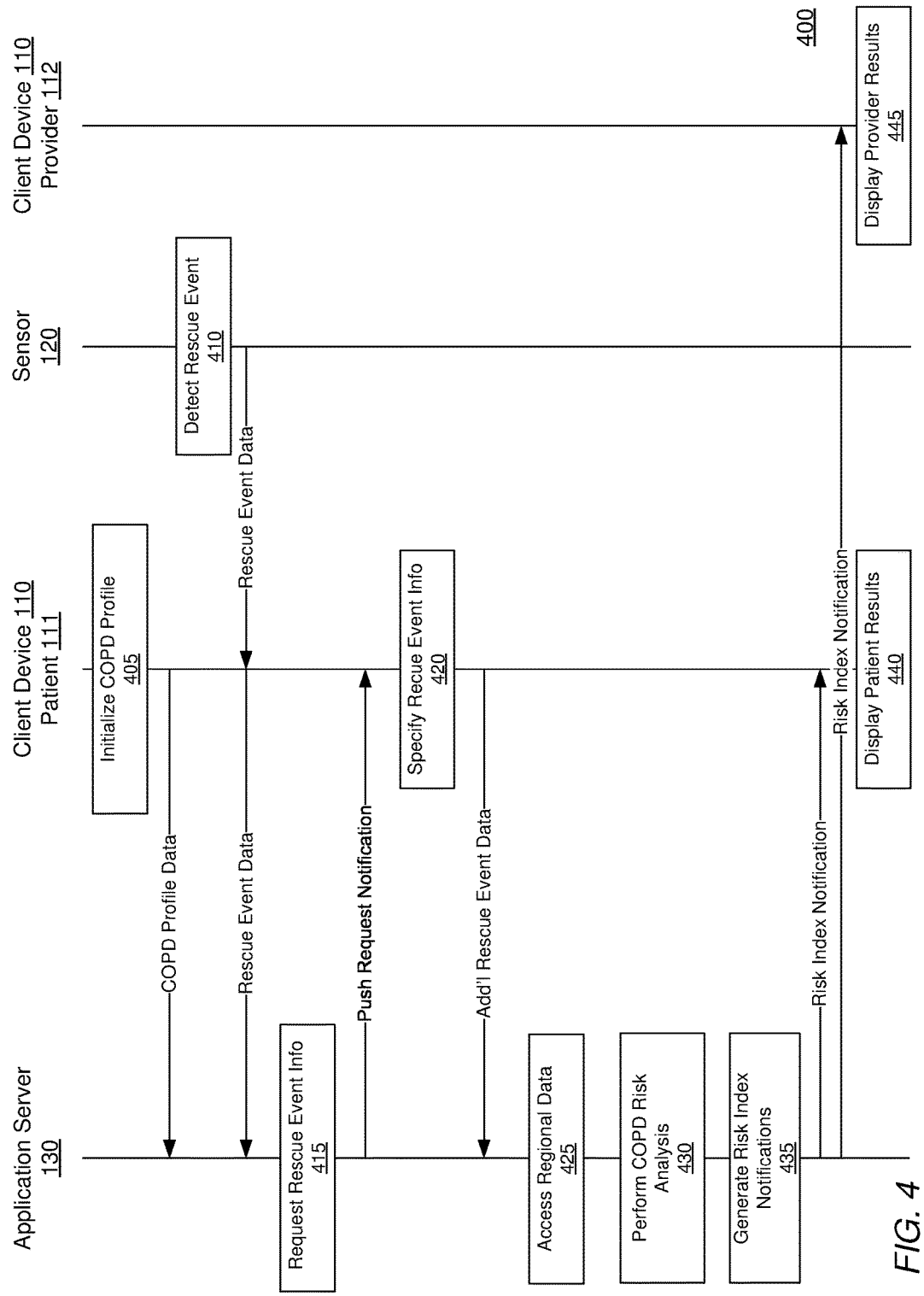
FIG. 4 shows an interaction diagram for providing COPD risk-based notifications based on medicament device monitoring, according to one embodiment.

FIG. 4 shows an interaction diagram for providing COPD risk notifications based on medicament device monitoring, according to one embodiment. As an initial step for generating COPD exacerbation risk notifications, a patient interfaces with the dashboard 300 to initialize 405 a patient profile. Once the patient is finished completing their patient profile, the client device 110 transmits the patient profile for use by the application server 130 and storage by the database server 140. Once a patient's patient profile is initialized 405, the application server 130 may begin to receive rescue medications events detected by the sensor 120 associated with the patient's medicament device 160.

Figure 5:
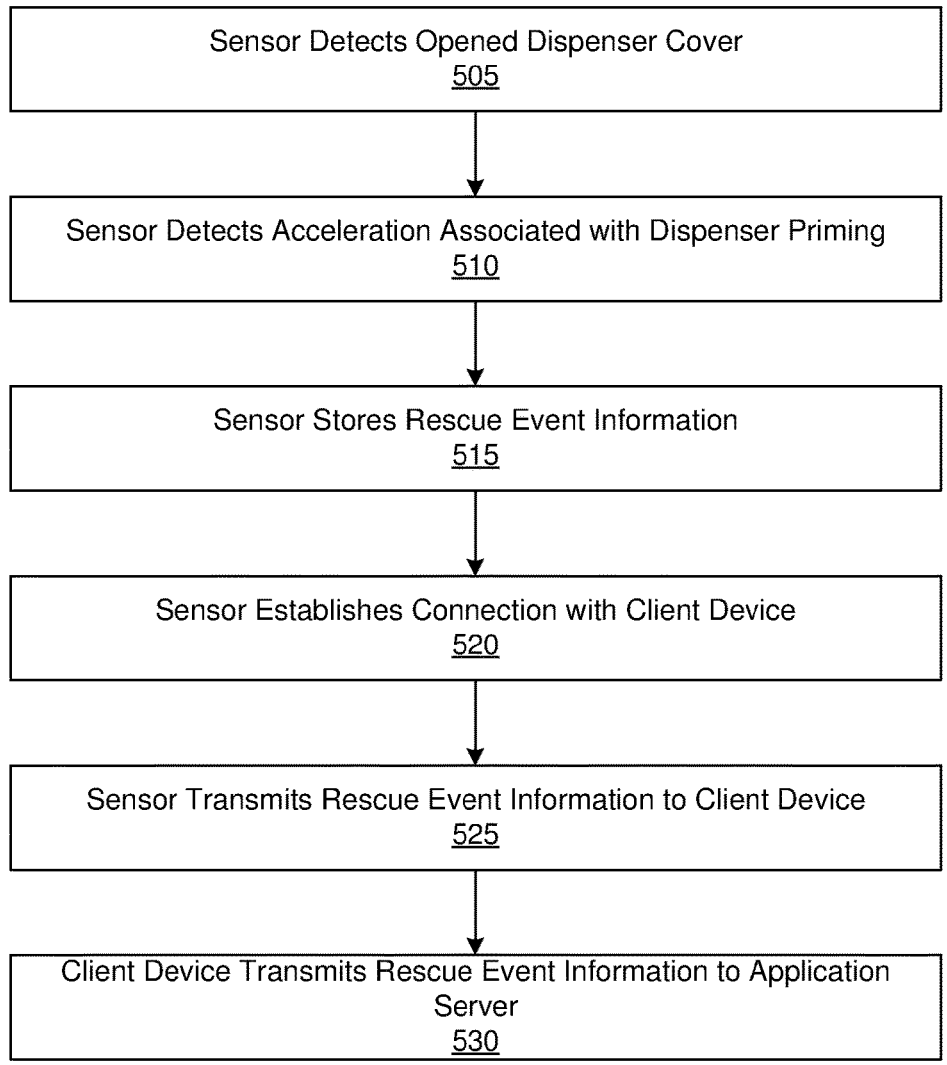
FIG. 5 shows a flowchart for detecting a rescue medication event by a COPD analytics system, according to one embodiment.

Referring now to FIG. 5, the application server 130 generally receives a rescue event anytime the patient uses their rescue medicament dispenser 160 to relieve difficulty breathing or other COPD symptoms. As an example of the process for capturing such an event for a particular device 160/sensor 120 combination, at the start of symptoms, the sensor 120 may detect 505 whether a medication dispenser 160 cover is opened. When the medication dispenser cover is opened, the sensor 120 may detect an acceleration 510 associated with a priming of the dispenser 160. For some types of medicament dispensers, the "priming" includes activating a mechanism to release a dose of a medication from a packaging. In other types of medicament dispensers, the "priming" includes a rapid shaking of a medication canister.

After the priming action is detected, the sensor 120 is configured to store 515 data associated with the rescue event in active memory of the sensor 120. The rescue event data may include information that describes the time and date of associated with the rescue event, the status or condition of the medicament device 160 (e.g. battery level), the number of doses of medication remaining (before or after the event), self-test results, and physiological data of a patient being treated with the medicament device 160 as measured by the sensor 120. As soon as the sensor establishes a network connection with either the client device 110 or network 150, the sensor transmits 525 any locally stored rescue event data to the client device 110 or the application server 130. If the event data was transmitted to the client device 110 first, the client device 110 then transmits 530 the rescue event data to the application server 130 as soon as the client device 110 establishes a network connection with the network 150. Depending upon the implementation, either the client device 110 or sensor 120 will add the geographic location where the event took place to the event data transmitted to the application server 130.

Returning now to FIG. 4, upon receiving the receiving the medication rescue event data, the application server 130 may request 415 further information from the patient describing the rescue medication event. To obtain the information, the application server 130 generates a push notification, including the questions to be asked, to be sent to the patient's client device 110. The client device 110 may present the push notification as a survey type card 310. The patient may respond to the request 415 by providing inputs 315 in response to the survey card 310, their input providing the additionally requested information 420 regarding the rescue event. The patient 111 may elect not to respond to the request 415. This is permissible, any gaps in information may be obtained through later push notifications, or upon entry by provider 112 after a meeting with the patient 111. In one implementation, the failure to receive the additionally requested data in response to request 415 does not hold up the remainder of the analysis described in steps 425-445.

Regarding the additional event data that is collected, the notification may specify 415, and the patient may provide 420, a list symptoms experienced during the rescue event, triggers that may have initiated the event such as exposure to smoke or outdoor air pollutants, a location of the rescue event, a label (e.g. work, home, school) for the location and a rating to signify the personal importance of the location to the patient, and whether medication use was pre-emptive (e.g., medication taken prior to exercising) in addition to any other relevant information. Card 310*j* illustrated in FIG. 3C is an example of a card that may be used to obtain the additional information 415.

In addition to requesting additional event data, the application server 130 accesses 425 stored regional data from the database server 140 regarding the geographic location where the rescue event took place. The application server 130 also accesses historical medication event data for the patient 111. This historical medication event data can include all of the data from any past controller or rescue medication event data from the patient's history over a variety of windows of time in the past, and each historical event may include all of the same items of information as was reported 410 for this event and collected 415/420 upon follow up thereafter. Further, each historical event may have been recorded using the real time process described in this section in conjunction with FIGS. 4-6. Thus, the historical data relied upon does not necessarily rely upon, although it may use, data manually collected or entered by a patient 111 or their health care provider 112, for example by interviews during patient visits with the provider 112.

IV.A Rescue Medication Trend

Figure 6:
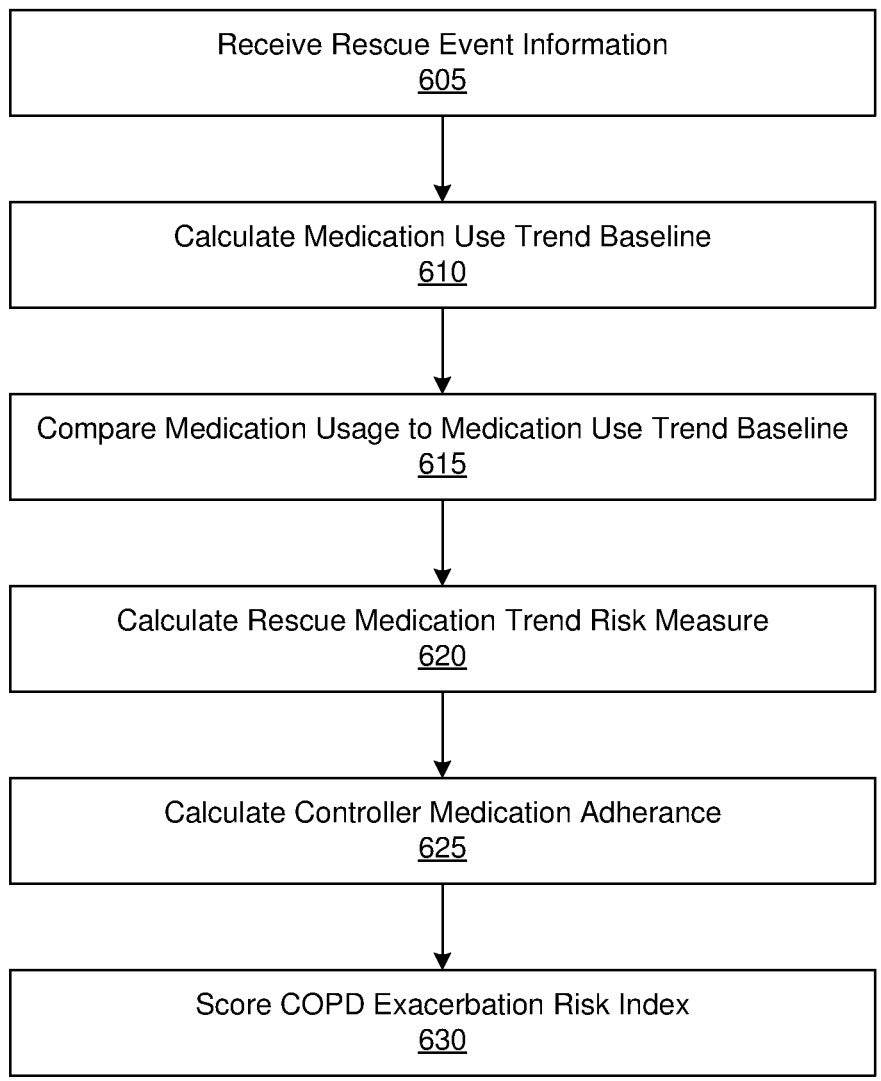
FIG. 6 shows a flowchart for providing a COPD risk analysis by a COPD analytics system, according to one embodiment.

The application server 130 performs a COPD risk analysis 430 to determine immediate changes in the patient's immediate condition, trends over time, and future COPD exacerbation risk. Referring now to FIG. 6, the data analysis module 131 receives 605 the rescue event data, historical rescue event data, historical controller event data, regional data, and the patient's profile. Using this historical data, the data analysis module 131 calculates 610 a rescue medication baseline for the patient 111 (or, simply, "baseline"). The baseline is used to determine whether the most recent medication event detected at step 410 has occurred more or less than a mean/median/mode of rescue medication events over some previous time window. Often the time window will start at the current time and date and extend backward in time, however in practice any previous window in time may be used.

The data analysis module 131 may calculate 610 the baseline according to any one variety of algorithms, one example of which is by summing each rescue medication event over the time window (e.g., a day, a week, two weeks, a month, longer) and dividing by the amount of time in the window (e.g., by the number of hours or days). In another example formula, the data analysis module 131 calculates the baseline by summing each rescue medication event over the preceding 29 days and dividing by the number of days that were measured. As an example calculation, if the data analysis module 131 receives fifty rescue medication events over twenty five individual days in the 29-day period, the calculated average value of the baseline would be two.

If there is less data available than the length of the time period over which the mean/median/mode is calculated, for example due to a patient profile having recently been created or rescue medications not having being tracked during the time window, the baseline may instead be calculated based on the number of days-worth of data that are available. In one implementation, if the number of days of data available is below a threshold (e.g., three), then the server 130 may decline to provide an analysis on the basis that there is not enough data available to establish a baseline, instead indicating that the server 130 is still in a learning period.

Although the baseline is described above as being determined with respect to a time window, in an alternate implementation, it may be determined based on the amount of time that has passed since a fixed number of rescue events have occurred, for example since the last 5 events. This alternate calculation is functionally equivalent to the calculation explained above, and can also provide a mean/median/mode representation of medication events for use in the COPD risk analysis.

The data analysis module 131 may also calculate a standard deviation for the rescue medication events over the time window. In one example, the standard deviation may be calculated according to:

$$s = \sqrt{\frac{1}{N-1}\sum_{i=1}^{N}(x_i - \bar{x})^2} \quad \text{Equation 1}$$

where s is the standard deviation, N is the number of days of data, $x_i$ is the number of rescue events on the i-th day, and x-bar is the average number of daily rescue events over all measured days.

The data analysis module 131 compares 615 the baseline against rescue medication events recorded over a more recent time window including the rescue medication event detected at step 410 to determine a trend in the patient's use of rescue medication (or "rescue medication trend"). Also here, the more recent time window generally extends backwards from the current date and time, though this is not necessarily always the case. In one implementation, if the number of rescue medication events over the more recent time window is below a threshold (e.g., four), then the data analysis module 131 may decline to perform the comparison on the basis that there is not enough data available to determine the rescue medication trend.

The comparison of step 615 may yield a determination that the patient is or is not at risk of an imminent COPD exacerbation based on one or more rules. In one implementation, if a patient exceeds a threshold number of rescue medication events during the more recent time window and the number of events exceeds the baseline for the more recent time window, the data analysis module 131 at least preliminarily labels the patient as being "at risk" for an imminent COPD exacerbation. For example, if the more recent time window is one day, and the threshold number of rescue medication events is ten, if a patient experiences ten rescue medication events during the day and the calculated baseline is less than ten, the data analysis module 131 at least preliminarily labels the patient as being "at risk" for an imminent COPD exacerbation. The module 131 stores this "at risk" rescue medication trend, and may further use the rescue medication trend in determining the risk score, described below.

Alternatively, if a patient does not experiences at least the threshold number of rescue medication events during the more recent time window or the number of events does not exceed the baseline for the more recent time window, the data analysis module 131 at least preliminarily labels the patient as being "not at risk" for an imminent COPD exacerbation. Continuing with the example above, if the patient experiences fewer than ten rescue medication events and/or if the calculated baseline is ten or greater, the data analysis module 131 at least preliminarily labels the patient as being "not at risk" for an imminent COPD exacerbation. The module 131 stores this "not at risk" rescue medication trend, and may further use the rescue medication trend in determining a risk score, described below.

The threshold number of rescue medication events may be a constant (e.g. 10) and may be a default value or a value specified by a user (e.g., a healthcare provider). Alternatively, the threshold number of rescue medication events may be a function of the historical data, the baseline, the standard deviation, or some combination thereof. In one example, the threshold, T, is given as:

$$T = B + \alpha s \quad \text{Equation 2}$$

where B is the calculated baseline described above, a is a numerical coefficient (example values, approximately 1.5), and s is the calculated standard deviation described above Additionally or alternatively, the data analysis module 131 may analyze more than one time window to determine a rescue medication trend. In one implementation, the data analysis module 131 examines two or more time windows to determine if a patient's rescue medication use is increasing over time. The data analysis module 131 may determine whether a count of rescue medication events of a more recent time window exceeds a count of rescue medication events of a second time window preceding the more recent time window. The data analysis module 131 may extend this comparison to any number of time windows, for example by determining whether a count of rescue medication events of the second time window exceeds a count of rescue medication events of a third time window, and so on. In one example, each time window is 24 hours, and the data analysis module 131 examines three time windows. If a patient experiences more rescue medication events in a more recent time window than a second time window that precedes the more recent time window, and more rescue medication events in the second time window that precedes a third time window, the data analysis module 131 at least preliminarily labels the patient as being "at risk" for an imminent COPD exacerbation, labels the patient as exhibiting a pattern of increasing rescue medication use, or both. The module 131 stores this pattern label, and may further use the pattern label to determine whether to label the patient as being "at risk" for an imminent COPD exacerbation, described below.

Determining that the patient exhibits a pattern of increasing rescue medication use may be combined with additional criteria to determine whether to label a patient as being "at risk" for an imminent COPD exacerbation. In one implementation, if a patient exhibits a pattern of increasing rescue medication use and the number of events for a more recent time window exceeds a threshold as described above, the data analysis module 131 at least preliminarily labels the patient as being "at risk" for an imminent COPD exacerbation. For example, if a patient exhibits a pattern of increasing rescue medication use over a 3 day period and the number of rescue events on the third day exceeds the threshold as defined in Equation 2, the data analysis module 131 at least preliminarily labels the patient as being "at risk" for an imminent COPD exacerbation.

In one implementation, the rescue medication trend is determinative of whether or what kind of COPD notification to send. The COPD notification is further described below with respect to FIG. 3H. In an alternative implementation, the rescue medication trend is one factor in a COPD exacerbation risk score (or simply "risk score") that is determinative of whether or what kind of COPD notification to send. Different users (e.g., patients and providers) may receive different COPD notifications. For example, providers may receive COPD notifications for any time period as they are calculated while patients may only receive COPD notifications from the preceding 24 hours. COPD notifications may be limited in other ways, such as limiting the number of COPD notifications per day (e.g., one per day). An alternative method for determining a rescue medication trend is described in U.S. Provisional Application 62,242,095, filed Oct. 15, 2015, at Section IV.A (paragraphs [0073]-[0078]).

The above paragraphs of this section describe several different techniques for determining a rescue medication trend and determining whether a patient should be labeled as at risk of a COPD event. These techniques are not mutually exclusive, and can be combined to provide multiple additive or alternative criteria for determining the rescue medication trend and/or determining a patient's at risk label.

IV.B Risk Score

The risk score is a mathematical function or process flow taking into account the rescue medication trend, and a controller medication adherence. Often, these two inputs are weighted such the rescue medication trend is more determinative of the risk score than the controller medication adherence, however this is not necessarily the case.

The controller medication adherence represents the extent of the patient's 111 adherence to taking their controller medication plan as prescribed by their health care provider 112, and as recorded as historical controller medication event data stored by the database server 140. The controller medication adherence, is based on the number of controller doses ingested by the patient 111 over some prior time window divided by the number of doses prescribed by the patient's health care provider 112 for that time window. In one embodiment, this time window is the previous week starting from the current day of the week. For example, if a patient is prescribed to take two doses of controller medication a day, the patient is therefore prescribed a total of fourteen doses for the week. If the patient has only taken seven doses of controller medication, then the controller medication adherence would be 50%. In other embodiments, other windows of time may be used to determine controller medication adherence.

In one implementation, module 131 determines the risk score by adding 80 points to the risk score if the patient's rescue medication trend is in the category of "not at risk" and by adding 0 points if the patient's rescue medication trend is in the category of "at risk". Module 131 further adds 0 points to the risk score if the controller medication adherence is less than 75%, and adds 20 points to the risk score if the controller medication adherence is between 75% to 100%.

If the application server 130 is not tracking the patient's controller medication usage and thus the controller medication adherence is not available, the patient is given the benefit of the doubt, and 20 points are added to the risk score. This helps reduce the number of false positive notifications that are sent out indicating that the patient is at risk of a COPD exacerbation when in fact the controller medication adherence was simply not available to be determined.

If the risk score is less than 79 points then the risk score indicates that 1) a rescue event has occurred 2) an increase in rescue medication events has occurred relative to the baseline and 3) that the patient is at a relatively "high" risk of COPD exacerbation. If the risk score falls between 80 and 99 points, the risk score indicates that 1) a rescue event has occurred and 2) the patient is at a relatively "moderate" risk of COPD exacerbation. If the risk score is 100, the risk score indicates that 1) a rescue event has occurred and 2) that the patient is at a relatively "low" risk of COPD exacerbation.

IV.C COPD Risk Notifications

Returning to FIG. 4, the application server 130 provides 430 either the rescue medication trend or the risk score as part of a notification to the patient 111, their healthcare provider 112, and/or any other authorized users. The notification may include rescue medication trend or the risk score itself as a numerical value (e.g., the amount of baseline or a value between 0 and 100, respectively), the risk categorization of either "at risk," "not at risk," "high," "moderate," or "low" risk of COPD exacerbation, as well as other information such as the amount the patient is over the baseline and/or the number of rescue medication events recorded by the system. FIG. 3H illustrates an example COPD exacerbation notification. In this example, the categorization provided to the patient is that the patient is "at risk" (and thus, this example illustrates that the recue medication trend is being used), that they are 50% over the baseline, and that they have used their rescue medication 10 times in the last 24 hours. Depending on whether the rescue medication trend or the risk score is used, the notification may or may not take into account controller medication use.

In addition to providing the COPD notification, the application server 130 may also send additional notifications in response to a detected rescue event 410. In one embodiment, such notifications include statistical and graphical information describing the rescue event, presented using information type cards 310 for display 435 in the dashboards 300 on the client devices 110. An example of such a card is illustrated in FIG. 3E, card 310c. The notifications may also include various permutations and combinations of time, location, temperature, humidity, and air quality index data regarding the geographic region in which the medication rescue event took place. This regional data may be presented in cards 310 as graphs, charts, lists, etc. An example of such a card is illustrated in FIG. 3B, card 310a.

For example, a patient 111 may be provided a geographical map with pinpoints of all of their medication rescue event locations that have occurred in the last year. As another example, a patient 111 may be provided with a geographical map include where event 410 took place, along with pinpoints of all medication rescue events that have occurred in the nearby geographical area either that day or within a threshold period of time, to indicate recent patterns in medication rescue events for that area. As another example, the healthcare provider 112 of the patient 111 may be presented with medication rescue event data from their patients 111 from that day or a recent period of time to help the provider 112 identify medication rescue event trends.

V. Benefits

The COPD risk notifications provided to patients 111 and providers 112 convey many benefits. Patients are informed of their risk of a COPD exacerbation and in real time or near real time (on the order of seconds to minutes), and can take action to prevent that occurrence, for example by improving their adherence to their controller medication, staying away from geographic areas with adverse conditions (e.g., pollution), adding or altering their prescribed medication regimen (such as an adjustment of dosage or the introduction of antibiotics or systemic corticosteroids), or scheduling an appointment with their doctor to address their recent spike in use of rescue medication which in turn would reduce the frequency of emergency room and hospital visits for the patient. Because the event data is automatically reported to the application server 130 without the need for patient input, the accuracy and quality of the event data is improved relative to manually-collected data by a health care provider 112 or other entity, and thus the accuracy of the conclusion for the risk of COPD exacerbation is also improved.

Additionally, follow up notifications provided by the application server 130 including reports of nearby rescue medication events by other patients can provide patients with additional information about others who are suffering from similar issues and provide regional information relevant for the patient's decision-making. Follow up notifications can further encourage the user regarding progress on taking their adherence medication. Ideally such notifications will prevent the occurrence of COPD exacerbations, thus preventing patient harm as well as hospital visits and their associated costs.

Health care providers informed of the risk of one or more of their patients' risk of COPD exacerbation can similar track the progress of their patients, and use the information to update their treatment regimen for each patient, schedule appointments with patients, and so on. For patients at high risk of a COPD exacerbation, the notification may be a call to action for the health care provider to communicate with the patient and encourage them to seek medical treatment. Follow up notifications may provide information about regional effects (e.g., pollution), patient controller medication adherence, etc.

VI. Additional Considerations

Although the discussion above focuses on COPD specifically, all systems and processes described herein are equally applicable to chronic respiratory disease (CRD) generally, and consequently can also be used to assist in treatment of CRD as well as COPD.

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A computer-executed method comprising:
receiving, by a remote server over a network, a plurality of rescue medication events from a plurality of client computing devices, each client computing device associated with a patient of a plurality of patients, wherein the plurality rescue medication events are detected by a sensor of a medicament device associated with each patient of the plurality of patients during a first time window;
storing, in a storage device of the remote server, the plurality of rescue medication events in association with a patient profile of each patient;
receiving, by the remote server over the network, a plurality of current rescue medication events at the remote server, wherein the current rescue medication events are detected by the sensor of the medicament device during a second time window occurring later in time than the first time window, wherein the plurality of current rescue medication events include a geographical location of the plurality of current rescue medication events recorded detected by the sensor;
responsive to receiving the plurality of current rescue medication events, applying, at the remote server, a machine-learned model to the plurality of rescue medication events and the current plurality of current rescue medication events together to determine a real-time risk of an outbreak of rescue medication usage for a geographic region; and
transmitting, by the remote server over the network, a real-time notification to the plurality of client computing devices associated with each patient, the real-time notification comprising the outbreak of rescue medication usage and information describing the one or more nearby rescue medication events in the geographical region.

2. The method of claim 1, applying, at the remote server, a machine-learned model to the plurality of rescue medication events and the plurality of current rescue medication events comprises:
determining a rescue medication baseline based on at least one historical rescue medication event for a plurality of patients in the geographic region;

determining a rescue medication trend by comparing the rescue medication baseline to a count of the current rescue medication events received during the second time window; and determining the real-time risk of the outbreak of rescue medication usage based on the rescue medication trend.

3. The method of claim 1, wherein the real-time notification comprises at least one of a numerical risk of outbreak of rescue medication usage, and a categorical risk of outbreak of rescue medication usage.

4. The method of claim 1, wherein the patient profile of each patient of the plurality of patients comprises an identifier of the client computing device associated with each patient.

5. The method of claim 1, wherein the patient profile of each patient of the plurality of patients comprises a type of controller medication and a type of rescue medication prescribed to the first patient.

6. The method of claim 2, wherein determining the rescue medication baseline comprises: summing a count of the historical rescue medication events occurring during the second time window; and dividing the count of the rescue medication events occurring during the second time window by a duration of the second time window.

7. The method of claim 5, wherein determining the rescue medication trend comprises: labeling the patient as at risk of rescue medication usage responsive to a function of the count of current rescue medication events received during the second time window and the rescue medication baseline being above a threshold value; and labeling the patient as not at risk of rescue medication usage responsive to the function of the count of current rescue medication events received during the second time window and the rescue medication baseline being below the threshold value.

8. The method of claim 1, further comprising:
storing, in the storage device of the remote server, a controller medication adherence plan for each patient;
receiving, over a third time window occurring earlier in time than the second time window, at least one historical controller medication event from the client computing device associated with each patient;
determining controller medication adherence based on the at least one historical controller medications event and the controller medication adherence plan; and
determining the real-time risk of rescue medication usage further based on the controller medication adherence.

9. The method of claim 8, wherein determining controller medication adherence comprises: dividing a count of the historical controller medication events occurring during the first time window by a number of controller medication doses prescribed in the controller medication adherence plan.

10. The method of claim 8, wherein determining the real-time risk of outbreak of rescue medication usage comprises: determining a numerical risk score based on the controller medication adherence and the rescue medication trend, wherein the controller medication adherence and the rescue medication trend are weighted relative to each other such that the rescue medication trend is more determinative of the numerical risk score than the controller medication adherence.

11. A non-transitory computer-readable storage medium comprising computer program instructions that, when executed by a computer processor, cause the computer processor to:
receive, by a remote server over a network, a plurality of rescue medication events from a plurality of client computing devices, each client computing device associated with of a plurality of patients, wherein the plurality of rescue medication events are detected by a sensor of a medicament device associated with each patient during a first time window;
store, in a storage device of the remote server, the plurality of rescue medication events in association with a patient profile of each patient;
receive, by the remote server over the network, a plurality of current rescue medication events at the remote server, wherein the current rescue medication events are detected by the sensor of the medicament device during a second time window occurring later in time than the first time window, wherein the plurality of current rescue medication events include a geographical location of the plurality of current rescue medication events recorded detected by the sensor;
responsive to receiving the plurality of current rescue medication events, apply, at the remote server, a machine-learned model to the plurality of rescue medication events and the current plurality of current rescue medication events together to determine a real-time risk of an outbreak of rescue medication usage for a geographic region; and
transmit, by the remote server over the network, a real-time notification to the plurality of client computing devices associated with each patient, the real-time notification comprising an outbreak of rescue medication usage and information describing the one or more nearby rescue medication events in the geographical region.

12. The storage medium of claim 11, wherein the instructions being configured to apply, at the remote server, a machine-learned model to the plurality of rescue medication events and the plurality of current rescue medication events comprises:
determining a rescue medication baseline based on at least one historical rescue medication event for a plurality of patients in the geographic region;
determining a rescue medication trend by comparing the rescue medication baseline to a count of the current rescue medication events received during the second time window; and
determining the real-time risk of the outbreak of rescue medication usage based on the rescue medication trend.

13. The storage medium of claim 11, wherein the real-time notification comprises at least one of a numerical risk of outbreak of rescue medication usage, and a categorical risk of outbreak of rescue medication usage.

14. The storage medium of claim 11, wherein the patient profile of each patient comprises an identifier of the client computing device associated with each patient of the plurality of patients.

15. The storage medium of claim 11, wherein the patient profile of the first patient comprises a type of controller medication and a type of rescue medication prescribed to each patient of the plurality of patients.

16. The storage medium of claim 12, wherein the instructions are further configured to:
store, in the storage device of the remote server a controller medication adherence plan for each patient;
receive, over a third time window occurring earlier in time than the second time window, at least one historical controller medication event from the client computing device associated with each patient;

determine controller medication adherence based on the at least one historical controller medications event and the controller medication adherence plan; and determine the real-time risk of rescue medication usage further based on the controller medication adherence.

17. The storage medium of claim 16, wherein the instructions being configured to determine controller medication adherence comprises: dividing a count of the historical controller medication events occurring during the first time window by a number of controller medication doses prescribed in the controller medication adherence plan.

18. The storage medium of claim 16, wherein the instructions being configured to determine the real-time risk of outbreak of rescue medication usage comprises: determining a numerical risk score based on the controller medication adherence and the rescue medication trend, wherein the controller medication adherence and the rescue medication trend are weighted relative to each other such that the rescue medication trend is more determinative of the numerical risk score than the controller medication adherence.

19. The storage medium of claim 16, wherein the instructions being configured to determine the rescue medication baseline comprises: summing a count of the historical rescue medication events occurring during the second time window; and dividing the count of the rescue medication events occurring during the second time window by a duration of the second time window.

20. The storage medium of claim 12, wherein the instructions being configured to determine the rescue medication trend comprises: labeling the patient as at risk of rescue medication usage responsive to a function of the count of current rescue medication events received during the second time window and the rescue medication baseline being above a threshold value; and labeling the patient as not at risk of rescue medication usage responsive to the function of the count of current rescue medication events received during the second time window and the rescue medication baseline being below the threshold value.

\* \* \* \* \*